US012569629B2

(12) United States Patent
Rawert et al.

(10) Patent No.: US 12,569,629 B2
(45) Date of Patent: Mar. 10, 2026

(54) INHALATION DEVICE SYSTEM

(71) Applicant: INVOX BELGIUM NV, Diepenbeek (BE)

(72) Inventors: Juergen Rawert, Cologne (DE); Steven Dudley, Brighton (GB)

(73) Assignee: INVOX BELGIUM NV, Diepenbeek (BE)

( * ) Notice: Subject to any disclaimer, the term of this patent is extended or adjusted under 35 U.S.C. 154(b) by 645 days.

(21) Appl. No.: 17/907,544

(22) PCT Filed: Mar. 29, 2021

(86) PCT No.: PCT/EP2021/058102
§ 371 (c)(1),
(2) Date: Sep. 28, 2022

(87) PCT Pub. No.: WO2021/198151
PCT Pub. Date: Oct. 7, 2021

(65) Prior Publication Data
US 2023/0142260 A1     May 11, 2023

Related U.S. Application Data

(60) Provisional application No. 63/002,812, filed on Mar. 31, 2020.

(30) Foreign Application Priority Data

Mar. 31, 2020    (EP) .................................... 20167228

(51) Int. Cl.
*A61M 15/00*        (2006.01)

(52) U.S. Cl.
CPC .... *A61M 15/0081* (2014.02); *A61M 15/0088* (2014.02); *A61M 2205/07* (2013.01)

(58) Field of Classification Search
CPC ............ A61M 11/0054; A61M 11/006; A61M 15/0081; A61M 15/0088; A61M 15/0065;
(Continued)

(56) References Cited

U.S. PATENT DOCUMENTS

| 5,447,150 A | 9/1995 | Bacon |
| 6,598,602 B1 | 7/2003 | Sjöholm |

(Continued)

FOREIGN PATENT DOCUMENTS

| EP | 0627230 B1 | 2/2000 |
| JP | 2019506261 A | 3/2019 |

(Continued)

OTHER PUBLICATIONS

International Search Report and Written Opinion of International Application PCT/EP2021/058102, Jun. 28, 2021, 12 pages.
(Continued)

*Primary Examiner* — Colin W Stuart
*Assistant Examiner* — Douglas Y Sul
(74) *Attorney, Agent, or Firm* — Synergy IP Group AG

(57) ABSTRACT

The invention provides an inhalation device system for the inhalative administration of a medically active liquid in nebulized form, the system comprising an inhalation device and an exchangeable reservoir for holding the medically active liquid, wherein the inhalation device comprises—a housing having a receiving unit, the receiving unit having a connection unit adapted to releasably and fluidically connect to a connection port of the exchangeable reservoir, the receiving unit being adapted to receive and fluidically connect to the exchangeable reservoir; —a nozzle for nebulization of the medically active liquid; and —a pumping unit arranged within the housing and adapted to be fluidically connected to the reservoir (via the connection unit of the receiving unit) and to the nozzle and being adapted to
(Continued)

convey (pressurize, pump) the medically active liquid in a downstream direction from the reservoir to the nozzle.

18 Claims, 4 Drawing Sheets

(58) Field of Classification Search
CPC .......... A61M 15/0068; A61M 2205/07; B05B 11/0035; B05B 11/0054
See application file for complete search history.

(56) References Cited

U.S. PATENT DOCUMENTS

| | | | |
|---|---|---|---|
| 6,988,496 B1 | 1/2006 | Eicher et al. | |
| 2001/0032643 A1 | 10/2001 | Hochrainer et al. | |
| 2004/0068222 A1 | 4/2004 | Brian | |
| 2005/0039738 A1 | 2/2005 | Zimlich et al. | |
| 2009/0216183 A1 | 8/2009 | Minotti | |
| 2012/0090603 A1 | 4/2012 | Dunne et al. | |
| 2012/0232474 A1 | 9/2012 | Nielsen et al. | |
| 2012/0260913 A1 * | 10/2012 | Bach .................... | B65D 83/384 |
| | | | 128/200.21 |
| 2012/0298694 A1 | 11/2012 | Holzmann | |
| 2017/0128680 A1 * | 5/2017 | Eicher ................. | A61M 11/006 |
| 2017/0361038 A1 * | 12/2017 | Mayer ............... | A61M 15/0025 |
| 2019/0001085 A1 | 1/2019 | Cottenden et al. | |
| 2020/0179620 A1 * | 6/2020 | Wuttke ................. | B05B 9/0822 |
| 2022/0135261 A1 * | 5/2022 | Eicher ................... | A61M 5/285 |
| | | | 53/471 |

FOREIGN PATENT DOCUMENTS

| | | | |
|---|---|---|---|
| RU | 2549310 C2 | 4/2015 | |
| WO | 9114468 A1 | 10/1991 | |
| WO | 2017076938 A2 | 5/2017 | |
| WO | WO-2018197730 A1 * | 11/2018 | ......... B05B 11/1091 |
| WO | 2019016409 A2 | 1/2019 | |

OTHER PUBLICATIONS

Frist Office Action issued in Russian Patent Application No. 2022122217, Jul. 19, 2024, 26 pages.

Office Action issued in Japanese Patent Application No. 2022554432, Nov. 12, 2024, 15 pages.

Second Office Action Issued in Russian Patent Application No. 2022122217, Nov. 15, 2024, 20 pages.

Office Action in parallel Chinese application 202180025436.4 dated Jan. 20, 2026.

\* cited by examiner

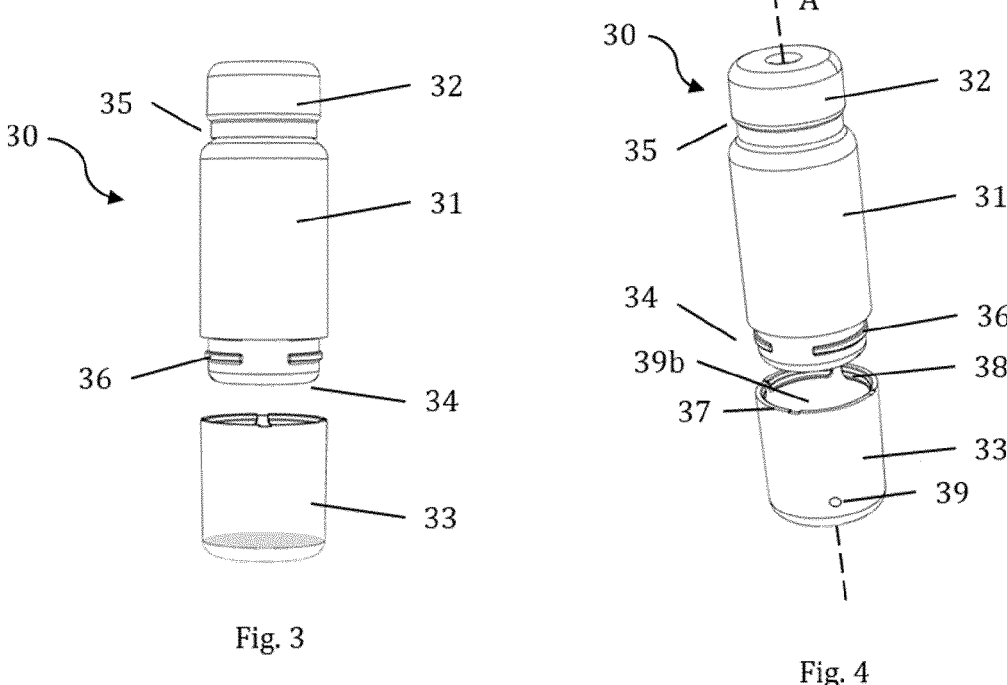
Fig. 3
Fig. 4
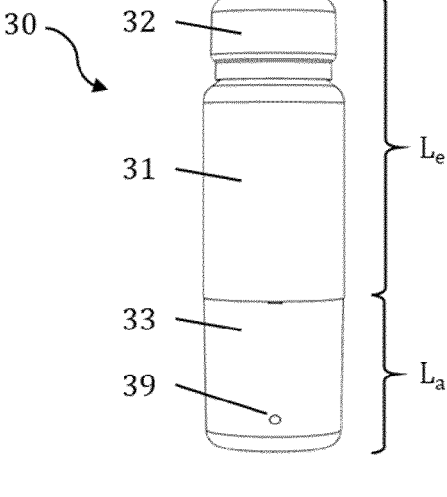
Fig. 5

INHALATION DEVICE SYSTEM

CROSS REFERENCE TO RELATED APPLICATIONS

This application is a United States National Stage Application filed under 35 U.S.C. § 371 claiming the benefit of PCT Application No. PCT/EP2021/058102, filed on Mar. 29, 2021, which claims priority to and the benefit of U.S. Provisional Application Ser. No. 63/002,812, filed on Mar. 31, 2020, and EP Application Serial No. 20167228.4, filed on Mar. 31, 2020, all of which are hereby incorporated by reference herein in their entireties.

FIELD OF THE INVENTION

The present invention relates to the field of inhalation devices for medically active liquids. In particular, the invention relates to an inhalation device system comprising an inhalation device and an exchangeable reservoir for holding a medically active liquid, wherein the exchangeable reservoir is provided in form of a cartridge system comprising a container portion and an extension element.

BACKGROUND OF THE INVENTION

Nebulizers or other aerosol generators for liquids have long been known from the art. Amongst others, such devices are used in medical science and therapy. There, they serve as inhalation devices for the application of active ingredients in the form of aerosols, i.e., small liquid droplets embedded in a gas. Such an inhalation device is known, e.g., from document EP 0 627 230 B1. Essential components of this inhalation device are a reservoir in which the liquid that is to be aerosolized is contained; a pumping device for generation of a pressure being sufficiently high for nebulizing the liquid; as well as an atomizing device in the form of a nozzle. By means of the pumping device, the liquid is drawn in a discrete amount, i.e., not continuously, from the reservoir and fed to the nozzle. The pumping device works without propellant and generates pressure mechanically.

A known embodiment of such an inhalation device is presented, e.g., in document WO 91/14468 A1. In such a device, the pressure in the pumping chamber which is connected to the housing is generated by movement of a moveable hollow piston. The piston is moveably arranged inside the immobile cylinder or pumping chamber. The upstream arranged inlet of the hollow piston is fluidically connected to the interior of the reservoir (i.e., reservoir pipe section). Its downstream arranged tip leads into the pumping chamber. Furthermore, a check valve that inhibits a back flow of liquid into the reservoir is arranged inside the tip of the piston.

A further inhalation device is known from WO 2018/197730 A1. The hand-held inhalation device disclosed therein comprises a housing having a user-facing side; an impingement-type nozzle for generating the nebulised aerosol by collision of at least two liquid jets, the nozzle being firmly affixed to the user-facing side of the housing such as to be immobile relative to the housing; a fluid reservoir arranged within the housing; and a pumping unit arranged within the housing, the pumping unit having an upstream end that is fluidically connected to the fluid reservoir and a downstream end that is fluidically connected to the nozzle. The pumping unit is adapted for pumping fluid from the fluid reservoir to the nozzle, and it comprises a riser pipe which is adapted to function as a piston in the pumping unit and is firmly affixed to the user-facing side of the housing such as to be immobile relative to the housing.

WO 2017/076938 A1 discloses a system with a nebulizer as well as a container with a fluid and an indicator device for such a nebulizer. A check scheme is used for indicating the number of containers already used with the nebulizer or which still can be used with the nebulizer. The indicator device indicates the number of uses performed or still possible with the current container.

WO 2019/016409 A2 discloses a nebulizer for nebulizing a liquid from a container and such a container. The nebulizer comprises a fluid pump for withdrawing the liquid in doses from the container and pressurizing the respective doses for nebulization. The container comprises an air pump with a piston/cylinder arrangement to pressurizing the liquid in the container to help withdrawing the liquid from the container. A control valve limits the air pressure acting on the liquid.

The known inhalation devices or inhalation device systems, however, can only be used with a specifically adapted exchangeable cartridge with fits into the inhalation device. Depending on the amount and nature of the medically active liquid or the medically active compound comprised therein, however, it may be desirable to provide for a system in which different exchangeable cartridges with different sizes and filling volumes may be inserted and used.

It is thus an object of the present invention to provide an inhalation device system that allows for the use of an exchangeable cartridge system that allows for the storage and administration of different volumes of medically active liquids in the same system. Further objects of the invention will be clear on the basis of the following description of the invention, examples and claims.

SUMMARY OF THE INVENTION

In a first aspect, the invention relates to an inhalation device system for the inhalative administration of a medically active liquid in nebulized form, the system comprising an inhalation device and an exchangeable reservoir for holding the medically active liquid, wherein the inhalation device comprises
    a housing having a receiving unit, the receiving unit having a connection unit adapted to releasably and fluidically connect to a connection port of the exchangeable reservoir, the receiving unit being adapted to receive and fluidically connect to the exchangeable reservoir;
    a nozzle for nebulization of the medically active liquid; and
    a pumping unit arranged within the housing and adapted to be fluidically connected to the reservoir and to the nozzle and being adapted to convey the medically active liquid in a downstream direction from the reservoir to the nozzle;
wherein
    the exchangeable reservoir is provided in form of a cartridge system having an overall volume $V_o$ and comprising a container portion having an effective volume $V_e$ for holding the medically active liquid and a connection port adapted to releasably and fluidically connect the cartridge system to the pumping unit, wherein the cartridge system further comprises an extension element having an additional volume $V_a$, the extension element being attached to the outer surface of the container portion.

In a second aspect, the present invention provides for an exchangeable cartridge system holding a medically active liquid for nebulization and preferably adapted for use in an inhalation device system according to the first aspect of the invention, wherein the cartridge system has an overall volume $V_o$ and comprises a container portion having an effective volume $V_e$ for holding the medically active liquid and a connection unit adapted to releasably and fluidically connect the cartridge system to the pumping unit of an inhalation device, wherein the cartridge system further comprises an extension element having an additional volume $V_a$, the extension unit being attached to the outer surface of the container portion.

In a third aspect, the present invention relates to a method for providing an exchangeable reservoir for an inhalation device system of the first aspect of the invention in the form of a cartridge system having an overall volume $V_o$, the method comprising the steps of a) providing a container portion having an effective volume $V_e$ for holding the medically active liquid the container portion comprising a connection port (preferably in form of a cap) adapted to releasably and fluidically connect the cartridge system to the pumping unit of the inhalation device system;

b) providing an extension element having an additional volume $V_a$; and c) attaching the extension element to the outer surface of the container portion.

BRIEF DESCRIPTION OF THE DRAWINGS

FIG. 3 depicts an exchangeable cartridge system having a container portion and an extension element in the disassembled state;

FIG. 4 shows a different perspective view of the cartridge system shown in FIG. 3;

FIG. 5 depicts an exchangeable cartridge system having a container portion and an extension element in the assembled state;

DETAILED DESCRIPTION OF THE INVENTION

Figure 1:
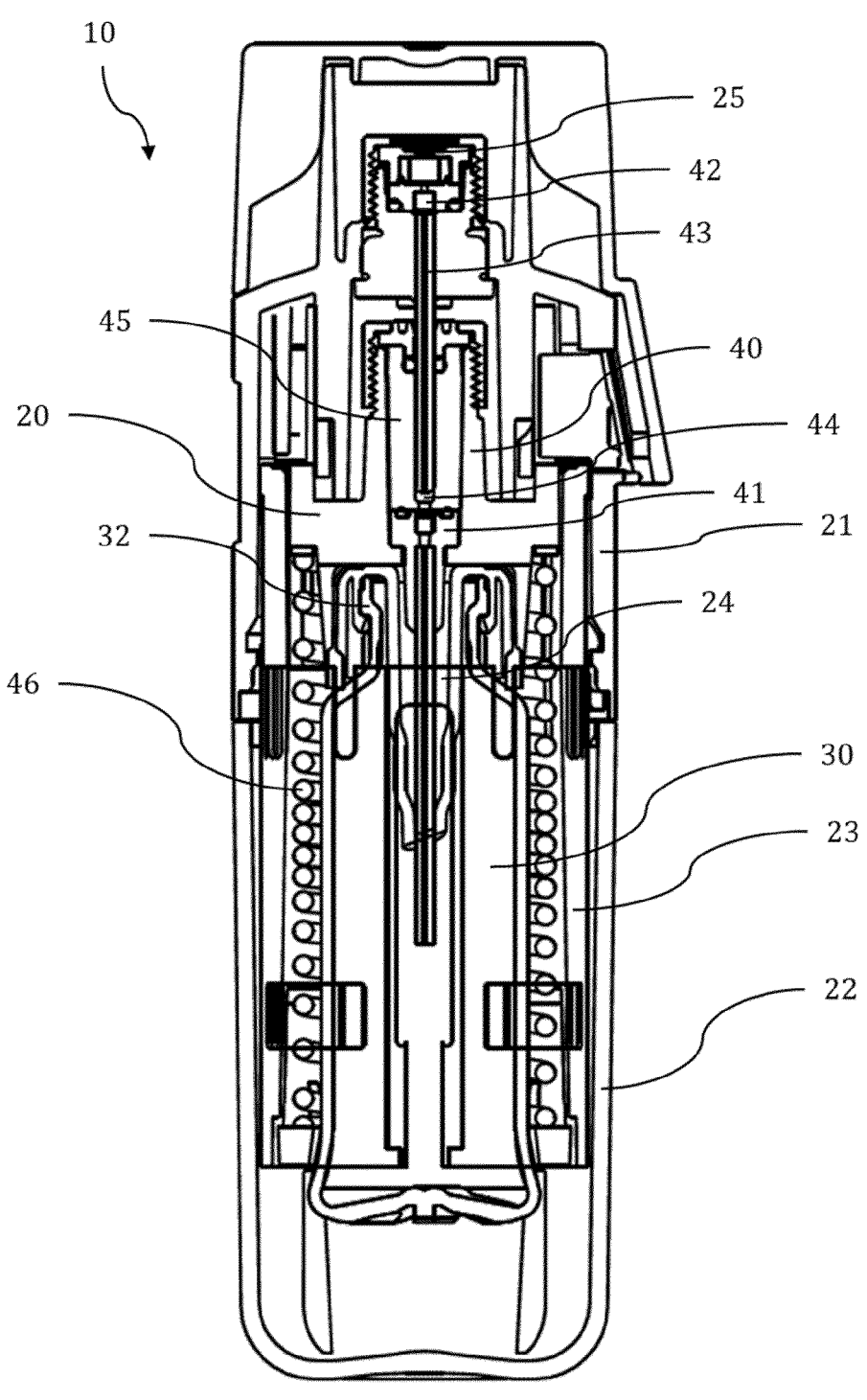
FIG. 1 depicts a cross-sectional view of an inhalation device system with a cartridge inserted into an inhalation device.

In a first aspect, the present invention provides an inhalation device system for the inhalative administration of a medically active liquid in nebulized form, the system comprising an inhalation device and an exchangeable reservoir for holding the medically active liquid, wherein the inhalation device comprises a housing having a receiving unit, the receiving unit having a connection unit adapted to releasably and fluidically connect to a connection port of the exchangeable reservoir, the receiving unit being adapted to receive and fluidically connect to the exchangeable reservoir;

a nozzle for nebulization of the medically active liquid; and a pumping unit arranged within the housing and adapted to be fluidically connected to the reservoir (via the connection unit of the receiving unit) and to the nozzle and being adapted to convey (pressurize, pump) the medically active liquid in a downstream direction from the reservoir to the nozzle; wherein the exchangeable reservoir is provided in form of a cartridge system having an overall volume $V_o$ and comprising a container portion having an effective volume $V_e$ for holding the medically active liquid and a connection port (preferably in form of a cap) adapted to releasably and fluidically connect the cartridge system to the pumping unit, wherein the cartridge system further comprises an extension element having an additional volume $V_a$, the extension element being attached to the outer surface of the container portion.

The inhalation device system according to the present invention is suitable for the inhalative administration of a medically active liquid in nebulized form, wherein the term "medically active liquid" as used herein refers to a liquid compound or composition that has pharmacological activity or which comprises a compound or composition which has pharmacological activity and which is capable to improve or prevent symptoms associated with diseases, disorders or conditions, specifically of a disease, disorder or condition of the respiratory system such as pulmonary diseases, disorders or conditions in a subject, specifically in a warm-blooded animal or human, especially in a human. Specific examples of such a disease, disorder or condition comprise, but are not limited to lung diseases or conditions such as asthma and/or chronic obstructive pulmonary disease (COPD), especially COPD, or interstitial lung diseases affecting the interstitium of the lung and lung tissues such as those associated with the air passages and/or air sacs (alveoli), for example pulmonary fibrosis such idiopathic pulmonary fibrosis (IPF), interstitial pneumonias, or sarcoidosis.

Furthermore, the term "inhalative administration" as used herein refers to a route of administration in which the medically active liquid is transported to the respiratory system, specifically to the lower respiratory system such as the lungs of a subject by inhalation of a stream of air other carrier gas comprising the medically active liquid in nebulized or aerosolized form by a subject. The terms "nebulized", "aerosolized" or "atomized" as used herein synonymously refer to a state of the medically active liquid in which it is present in the form of an aerosol having at least two phases: a continuous phase which is gaseous, such as air or another carrier gas, and which comprises a dispersed liquid phase in the form of small liquid droplets, and a liquid phase, i.e. the medically active liquid, which may itself represent a liquid solution, dispersion, suspension, or emulsion. In specific embodiments, such an aerosol has respirable particles or droplets, preferably having a mass median aerodynamic diameter (as measured by laser diffraction) of not more than about 10 μm, in particular not more than about 7 μm, or not more than about 5 μm, respectively.

In specific embodiments, the term "medically active liquid" as used herein refers to a medically active liquid in form of a pharmaceutical composition comprising at least one active pharmaceutical ingredient (API), more specifically at least one inhalable active pharmaceutical ingredient. More specifically, such at least one inhalable active pharmaceutical ingredient may, for example, be selected from long-acting muscarinic antagonists (LAMA), long-acting beta agonists (LABA) and inhalable glucocorticosteroids (ICS), as well as from analgetics and antidiabetics, either alone or in combination which each other.

Examples for long-acting muscarinic antagonists (LAMA) comprise, but are not limited to aclidinium bromide, glycopyrronium salts, such as glycopyrronium bromide, revefenacin, tiotropium, such as tiotropium bromide, umeclidinium bromide, oxitropium bromide, flutropium bromide, ipratropium bromide, trospium chloride, tolterodine.

Examples for long-acting beta agonists (LABA) comprise, but are not limited to, albuterol, arformoterol, bambuterol, bitolterol, broxaterol, carbuterol, clenbuterol, fenoterol, formoterol, hexoprenaline, ibuterol, indacaterol, indacterol, isoetharine, isoprenaline levosalbutamol, mabuterol meluadrine, metaproterenol, olodaterol, orciprenaline, pirbuterol, procaterol, reproterol, rimiterol, ritodrine, salmeterol, salmefamol, soterenot, sulphonterol, tiaramde, terbutaline, terbuterol.

Examples of inhalable glucocorticosteroids (ICS) comprise, but are not limited to, prednisolone, prednisone, butixocort propionate, flunisolide, beclomethasone, triamcinolone, budesonide, fluticasone, mometasone, ciclesonide, rofleponide, dexamethasone, etiprednol-dichloroacetat, deflazacort, etiprednol, loteprednol, RPR-106541, NS-126, ST-26.

Furthermore, active pharmaceutical ingredients may be selected from analgetics, such as opioid analgetics (e.g. morphine, fentanyl) or non-opioid analgetics (e.g. salicylic acid derivates, e.g. acetylsalicylic acid) or cannabinoids (e.g. tetrahydrocannabinol), antidiabetics, such as insulin.

The medically active liquid or liquid pharmaceutical composition that may be nebulized or aerosolized by the present inhalation device system may comprise at least one active pharmaceutically ingredient as described above but may also comprise a mixture of two or more active pharmaceutically ingredients that may be administered by inhalation.

The medically active liquid or pharmaceutical composition that may be aerosolized by the inhalation device system according to the invention is preferably formulated as a composition that is suitable, and adapted for inhalative use, in other words a composition that may be nebulized or aerosolized for inhalation and that is physiologically acceptable for inhalation by a subject.

The medically active liquid or pharmaceutical composition that may be administered by the present inhalation device system or that may by contained within the corresponding exchangeable reservoir may be in the form of a dispersion, for example a suspension with a liquid continuous phase, and a solid dispersed phase or in the form of a solution.

In further embodiments, the medically active liquid or pharmaceutical composition as described above may comprise, optionally, one or more physiologically acceptable excipients, which are suitable for inhalative use. Excipients which may be featured in the composition may include, but are not limited to, one or more buffering agents to regulate or control pH of the solution, salts, taste-masking agents, surfactants, lipids, antioxidants, and co-solvents, which may be used to enhance or improve solubility, for example ethanol, or a glycol.

In specific embodiments, the medically active liquid as described above may be essentially free of a propellant, such as a hydrofluoroalkane (HFA) propellant.

In further specific embodiments, the medically active liquid as described above may be an aqueous solution, in which one or more active pharmaceutical ingredients as described above are dissolved and solubilized in a liquid carrier solution comprising water. Such aqueous solutions optionally may also comprise one or more excipients as described above.

The inhalation device system of the present invention comprises an inhalation device and an exchangeable reservoir for holding the medically active liquid. The inhalation device of the inhalation device system of the present invention, in specific embodiments, may be a hand-held device or, in other words, a mobile device which can be conveniently held in and used with one hand and which is suitable for delivering a nebulised medically active aerosol as described above for inhalation therapy. In order to be suitable for inhalation therapy, the device must be able to emit a medically active aerosol whose particle size is respirable, i.e., small enough to be taken up by the lungs of a patient or user with respirable particles in the above-described range. In this respect, inhalation devices are substantially different from devices that emits spray for oral or nasal administration, such as disclosed in US 2004/0068222 A1.

The inhalation device of the present system comprises a housing which defines the outer casing of the inhalation device, specifically the outer casing in which the further components of the inhalation device are received and/or attached to. The housing may have a user-facing side which can be contacted by the user of the inhalation device, specifically for inhalative administration as described above. In specific embodiments, the user facing side may be a mouthpiece that may be introduced to the mouth of the user, specifically for inhalation or administration of the nebulized medically active liquid. Furthermore, the housing may have a lower part, preferably located at the upstream end of the inhalation device, that can be detached and at least partly removed to open the housing and allow access to a receiving unit into which the exchangeable cartridge can be inserted. The term "upstream" as used herein means, with regard of the present inhalation device, inhalation device system, cartridge system or other component the direction or location from which the medically active liquid is conveyed by the inhalation device during operation. In contrast to this, the term "downstream" as used herein means the opposite direction or location to which the medically active liquid is conveyed by the inhalation device during operation. The inhalation device, or more specifically, the housing of the present inhalation device comprises a receiving unit adapted to receive an exchangeable reservoir or cartridge system as described in further detail below. The receiving unit has a connection unit adapted to releasably and fluidically connect to a connection port of the exchangeable reservoir. The term "fluidically connect" as used herein means that with regards to two elements a connection, preferably a gas-tight and/or liquid-tight connection is established or may be established that allows for the transfer of the fluid such as a gas or liquid from one element to the other, preferably in a way in which such fluid is completely transferred from one element to the other.

The receiving unit of the housing is adapted to receive or, in some embodiments, to fully receive and fluidically connect to the exchangeable reservoir as described in further detail below. This means, especially with regard to the term "fully received" as used herein, that such exchangeable reservoir may be completely introduced into the receiving unit of the housing such that the receiving unit and the housing may completely enclose or encase the exchangeable reservoir, preferably in a way that when introduced into the receiving unit the surface of the exchangeable reservoir is completely enclosed by the housing of the inhalation device.

The inhalation device of the system of the present invention further comprises a nozzle for the nebulization of the medically active liquid. The person of skill in the art knows different kinds of nozzles which are suitable for the nebulization, aerosolization or atomization of the medically active liquid to be administered by the system of the present invention, such as impingement-type nozzles, swirl nozzles, orifice nozzles, surface impinging nozzles or multi-fluid nozzles. In specific embodiments, however, the nozzle of the present inhalation device is of the impingement type. This means that the nozzle is adapted to emit at least two jets of liquid which are directed such as to collide and break up into small aerosol droplets. In specific embodiments, the nozzle is firmly affixed to the housing, especially to the user-facing side of the housing of the inhalation device in such a way that it is immobile, or non-moveable, relative to the housing or at least relative to the side or part of the housing which faces the user (e.g., patient) or which, more specifically, is introduced to the mouth of a user when the device is used.

The inhalation device of the system of the present invention further comprises a pumping unit which is arranged within the housing of the inhalation device. The pumping unit is adapted to be fluidically connected to the reservoir, specifically via the connection unit of the receiving unit. In specific embodiments, the pumping unit is fluidically connected to the reservoir via the connection unit of the receiving unit. Furthermore, the pumping unit is also adapted to be fluidically connected to the nozzle or, in specific embodiments, is connected to the nozzle, and is furthermore adapted to convey or, in other words, pump the medically active liquid in a downstream direction from the reservoir to the nozzle.

The pumping unit as comprised by the inhalation device of the present invention, in specific embodiments, is suitable for and adapted to deliver the nebulised medically active liquid in a discontinuous manner, i.e., in the form of discrete units, wherein one unit is delivered per pumping cycle. In this aspect, the inhalation device differs from commonly known nebulisers such as jet nebulisers, ultrasonic nebulisers, vibrating mesh nebulisers, or electrohydrodynamic nebulisers which typically generate and deliver a nebulised aerosol continuously over a period of several seconds up to several minutes, such that the aerosol requires a number of consecutive breathing manoeuvres in order to be inhaled by the patient or user. Instead, the inhalation device of the present invention is adapted to generate and emit discrete units of aerosol, wherein each of the units corresponds to the amount (i.e., volume) of fluid (i.e., medically active liquid) which is pumped by the pumping unit in one pumping cycle into the nozzle where it is immediately aerosolised and delivered to the user or patient. Vice versa, the amount of liquid pumped by the pumping unit in one pumping cycle determines the amount of the pharmacologically active agent which the patient receives per dosing. It is therefore highly important with respect to achieving the desired therapeutic effect that the pumping unit operates precisely, reliably and reproducibly. Such inhalation devices exhibiting high precision and reproducibility, specifically incorporating a pumping unit as described in further detail below, are known to those of skill in the art and are described in WO 2018/197730 A1 the disclosure of which is incorporated herein in its entirety. It should be noted however, that the specific design of the pumping unit may be varied and that further pumping units, such as the unit described in US 2012/0090603 A1, which is incorporated herein by reference in its entirety, may also be used in the inhalation device of the present invention.

In specific embodiments, the pumping unit may be also arranged within the housing and may be adapted to function as a piston pump, also referred to as plunger pump, wherein a riser pipe functions as the piston, or plunger, which is longitudinally moveable within a hollow cylinder. The pumping unit may have an upstream end that is fluidically connected to the exchangeable reservoir and a downstream end that is fluidically connected to the nozzle. In further specific embodiments, the pumping unit may comprise a riser pipe which may be adapted to function as a piston in the pumping unit, a hollow cylinder and a lockable means for storing potential energy. The lockable means may be capable of storing potential energy when locked and may be adapted for releasing the stored energy when unlocked, such as a spiral spring or other elastic element. The lockable means may be arranged outside of and mechanically coupled to the hollow cylinder in such a way that unlocking the means results in a propulsive longitudinal movement of the cylinder towards the downstream end of the pumping unit. The inner segment of such a hollow cylinder in which the upstream end of such riser pipe moves forms a pumping chamber which has a variable volume, depending on the position of the riser pipe relative to the cylinder.

The hollow cylinder which provides the pumping chamber may be fluidically connected to the exchangeable reservoir, or more specifically to the connection port of the exchangeable reservoir, either directly or indirectly, such as by means of an optional reservoir pipe (or reservoir pipe section). Similarly, the riser pipe, whose reservoir-facing, interior (upstream) end which can be received in the hollow cylinder, may be fluidically connected at its downstream or exterior end to the nozzle in a liquid-tight manner, either directly or indirectly.

In this context, the expression "hollow cylinder" refers to a part or member which is hollow in the sense that it comprises an internal void which has a cylindrical shape, or which has a segment having a cylindrical space. In other words, and as is applicable to other types of piston pumps, it is not required that the external shape of the respective part or member is cylindrical. Moreover, the expression "hollow cylinder" does not exclude an operational state of the respective part or member in which the "hollow" space may be filled with material, e.g., with a liquid to be nebulised.

As used herein, a longitudinal movement is a movement along the main axis of the hollow cylinder, and a propulsive movement is a movement of a part in a downstream (or forward) direction.

In specific embodiments, the riser pipe of the pumping unit of the inhalation device of the invention may be arranged downstream of the cylinder and may be firmly affixed to the user-facing side of the housing such as to be immobile relative to the housing or at least to the part of the housing which comprises the user-facing side of the housing. For the avoidance of doubt, the term "firmly affixed" means either directly or indirectly (i.e., via one or more connecting parts) affixed such as to prevent relative movement between the respective parts. As the nozzle preferably is also immobile relative to the housing or the respective part of the housing, the riser pipe preferably is also immobile relative to the nozzle, and the pumping action, in these embodiments, is effected by the longitudinal movement of the hollow cylinder. A propulsive movement of the cylinder, which in this embodiment is arranged in an upstream position relative to the riser pipe, results in a decrease of the volume of the pumping chamber, and a repulsive movement of the cylinder results in an increase of the volume. In other words, in these embodiments, the riser pipe maintains its position relative to the housing, and the hollow cylinder can alter its position relative to the housing, and in particular, along a longitudinal axis of the same, such as to perform a piston-in-cylinder-type movement of the immobile riser pipe in the moveable cylindrical member.

This arrangement differs from other impingement-type inhalation devices which rely on a pumping unit whose riser pipe is in an upstream position and a cylindrical member in a downstream position wherein the riser pipe is moveable and the cylindrical member is fixed to the housing, as disclosed in US 2012/0090603 A1. A key advantage of the device having a fixed raiser pipe as described above is that the passage between pumping chamber and exchangeable reservoir can be designed with less restrictions with respect to its dimensions. It is possible to accommodate a signifi-cantly larger inlet valve (also referred to as check valve), which is easier to manufacture since it does not have to be contained within a narrow riser pipe. Instead, the fixed riser pipe design of the pumping unit allows for the use of a check valve whose size is only restricted by the interior size of the housing or the dimensions of the means for storing potential energy. In other words, the diameters of the valve, the riser pipe and—if used—the reservoir pipe do not need to match to each other. Furthermore, since in this embodiment no movable piston needs to be connected to the exchangeable reservoir, the component which provides the fluid connec-tion to the reservoir can be designed independently of the moveable component, i.e., the hollow cylinder, allowing the individual parts to be adapted to suit their respective indi-vidual functions. In this respect, the fixed riser pipe design according to this specific embodiment provides for higher design flexibility because the moveable hollow cylinder, due to its robust structure and dimensions, provides better oppor-tunities for designing a mechanically stable connection with the reservoir than would a less robust moveable riser pipe. Also, in this embodiment, the connection between the hol-low cylinder and the exchangeable reservoir can be designed with a larger diameter, such that higher flow velocities and fluid viscosities become feasible. Further, a support for the exchangeable reservoir can be integrated into any compo-nent that comprises the cylinder. Additionally, in this embodiment, any vent for pressure equilibration of the exchangeable reservoir can be moved away from the reser-voir body itself to, for example, a connector which forms an interface between exchangeable reservoir and hollow cylin-der of the pumping unit, thus facilitating construction and avoiding the necessity to provide an essentially "open" reservoir body. This is especially important in cases in which the reservoir is designed as an exchangeable reservoir as it is the case in the present invention.

As mentioned above, the lockable means for storing potential energy may be adapted to store energy in its locked state and to release the stored energy when unlocked. In specific embodiments, the lockable means is mechanically coupled to the hollow cylinder in such a way such that unlocking the means results in a propulsive longitudinal movement of the hollow cylinder towards the downstream end of the pumping unit. During this movement, the internal volume of the cylinder, i.e., the volume of the pumping chamber, decreases. Vice versa, when the means for storing potential energy is in the locked state, the hollow cylinder is in its most upstream position in which the volume of the pumping chamber is largest. The locked state could also be considered a primed state. When the state of the means for storing energy is altered from the unlocked to the locked state, which could be referred to as priming the device, the hollow cylinder performs a repulsive longitudinal movement, i.e., from its most downstream position towards its most upstream position. A pumping cycle consists of two subsequent and opposing movements of the hollow cylinder starting from its most downstream position to its most upstream (or primed) position and—driven by the lockable means for storing potential energy that now releases its energy—back to its most downstream position.

In specific embodiments, the pumping unit is a high-pressure pumping unit and adapted to operate, or to expel fluid, at a pressure of at least about 50 bar. In other preferred embodiments, the operating pressure of the pumping unit is at least about 10 bar, or at least about 100 bar, or from about 2 bar to about 1000 bar, or from about 50 bar to about 250 bar, respectively. As used herein, the operating pressure is the pressure at which the pumping unit expels the medically active liquid to be administered, such as an inhalable aque-ous liquid formulation of a pharmacologically active ingre-dient, from its pumping chamber in a downstream direction, i.e., towards the nozzle. In this context, the expression "adapted to operate" means that the components of the pumping unit are selected with respect to the materials, the dimensions, the quality of the surfaces and the finish are selected such as to enable operation at the specified pressure.

Moreover, such high-pressure pumping unit implies that the lockable means for storing potential energy is capable of storing and releasing a sufficient amount of energy to drive the propulsive longitudinal movement of the cylinder with such a force that the respective pressure is obtained.

The lockable means for the storage of potential energy may be designed as a tension or pressure spring. Alterna-tively, besides a metallic or plastic body, also a gaseous medium, or magnetic force utilizing material can be used as means for energy storage. By compressing or tensioning, potential energy is fed to the means. One end of the means may be supported at or in the housing at a suitable location; thus, this end is essentially immobile. With the other end, it may be connected to the hollow cylinder of the pumping unit which provides the pumping chamber; thus, this end may be essentially moveable. The means for the storage of potential energy can be locked after being loaded with a sufficient amount of energy, such that the energy can be stored until unlocking takes place. When unlocked, the means can release the potential energy (e.g., spring energy) to the cylinder with the pumping chamber, which is then driven such as to perform a (in this case, longitudinal) movement. Typically, the energy release takes place abruptly, so that a high pressure can build up inside the pumping chamber before a significant amount of medically active liquid is emitted, which results in a pressure decrease. In fact, during a significant portion of the ejection phase, an equilibrium exists of pressure delivered by the means for the storage of potential energy, and the amount of medically active liquid already emitted. Thus, the amount of medically active liquid remains essentially constant during this phase, which is a significant advantage to devices which use manual force of the user for the emission, such as the devices disclosed in documents US 2005/0039738 A1, US 2009/0216183 A1, US 2004/0068222 A1, or US 2012/0298694 A1, since manual force depends on the individual user or patient and is very likely to vary largely during the ejection phase, resulting in heterogeneous droplet formation, size, and amount. In con-trast to the prior art, the means according to the invention ensures that the inhalation device delivers highly reproduc-ible results.

In further embodiments, the means for storing potential energy may also be provided in the form of a highly pressurized gas container. By suitable arrangement and repeatable intermittent activating (i.e., opening) of the same, part of the energy which is stored inside the gas container can be released to the cylinder. This process can be repeated until the remaining energy is insufficient for once again building up a desired pressure in the pumping chamber. After this, the gas container must be refilled or exchanged.

In specific embodiments, the lockable means for storing potential energy is a spring having a load of at least 10 N in a deflected state. In preferred embodiments, the means for storing potential energy is a compression spring made of steel having a load from about 1 N to about 500 N in its deflected state. In other preferred embodiments, the compression spring from steel has a load from about 2 N to about 200 N, or from about 10 N to about 100 N, in its deflected state.

In one preferred embodiment, a single dose of the medication (i.e., of the nebulised aerosol of the medically active liquid) is contained in one unit, i.e., in the volume that is delivered from the pumping unit to the nozzle for aerosol generation in one single pumping cycle. In this case, the user or patient will prime and actuate the device only once, and inhale the released aerosol in one breathing manoeuvre, per dosing (i.e., per dosing event).

In another preferred embodiment, a single dose of the medication consists of two units of the aerosol, and thus requires two pumping cycles. Typically, the user or patient will prime the inhalation device, actuate it such as to release and inhale a unit of the aerosol, and then repeat the procedure. Alternatively, three or more aerosol units may constitute a single dosing.

The volume of fluid (e.g., of medically active liquid) that is pumped by the pumping unit of the present inhalation device system in one pumping cycle may be preferably in the range from about 0.1 μL to about 1000 μL, or from about 1 μL to about 250 μL, or from about 2 μL to about 150 μL. In particular, the volume may range from about 2 μL to about 50 μL, or from about 5 μL to about 25 μL, more specifically of from about 10 μL to about 20 μL, such as about 15 μL. These volume ranges are nearly the same as the volume of liquid phase that is contained in one unit of aerosol generated by the inhalation device, perhaps with minor differences due to minute losses of liquid in the device.

In further specific embodiments, the pumping unit of the inhalation device comprises an inlet valve, also referred to as a check valve or inlet check valve, positioned in the hollow cylinder. According to this embodiment, the interior space of the hollow cylinder, i.e., the pumping chamber, is fluidically connected with the fluid reservoir via the inlet check valve. The inlet valve allows the inflow of liquid into the pumping chamber, but prevents the backflow of medically active liquid towards, or into, the exchangeable fluid reservoir. In preferred embodiments, the position of the inlet valve may be at or near the upstream end of the cylinder such as to make nearly the entire internal volume of the hollow cylinder available for functioning as the pumping chamber. Alternatively, it may be more centrally located along the (longitudinal) main axis of the hollow cylinder such as to define an upstream segment and a downstream segment of the cylinder, the upstream segment being upstream of the inlet valve and the downstream segment being downstream of the valve. In this case, the pumping chamber is located in the downstream segment.

As mentioned, one of the advantageous effects of the specific embodiment of the pumping unit having a fixed or immobile piston as described above is that an inlet valve having relatively large dimensions may be accommodated in this position, i.e., at the upstream end of the pumping chamber. This is particularly beneficial as it allows for large dimensions of the fluid conduit(s) within the valve, thus enabling high fluid velocities which translate into a rapid filling of the pumping chamber during the priming of the inhalation device. Moreover, the use of medically active liquids having a higher viscosity than ordinary liquid formulations for inhalation, such as highly concentrated solutions of soluble active ingredients, become feasible for inhalation therapy.

In further embodiments, the inlet valve may be adapted to open only when the pressure difference between the upstream and the downstream side of the valve, i.e., the fluid reservoir side and the pumping chamber side, is above a predefined threshold value, and remains closed as long as the pressure difference is below the threshold value. In this context, the term "pressure difference" means that, irrespective of the absolute pressure values, only the relative pressure difference between the two sides is relevant for determining whether the valve blocks or opens. If, for example, the pressure on the upstream (reservoir) side is already positive (e.g., 1.01 bar due to thermal expansion), but the pressure on the downstream (pumping chamber) side is ambient pressure (e.g., 1.0 bar, no activation of the device), the pressure difference (here: 0.01 bar) is below the threshold value (e.g., 20 mbar), which allows the valve to stay closed even when subject to a positive pressure in opening direction. This means that the check valve remains closed until the threshold pressure is met, thus keeping the passage between reservoir and pumping chamber safely shut, e.g., when the inhalation device is not in use. Examples for threshold pressure differences are in the range of 1 to 1000 mbar, and more preferably between about 10 and about 500 mbar, or between about 1 and about 20 mbar.

When actuating the inhalation device of the present inhalation device system, as the means for storing potential energy alters its state from a locked state to an unlocked state, energy is released which effects the cylinder to perform its propulsive longitudinal movement, significant pressure is built up in the pumping chamber. This generates a marked pressure difference due to a high pressure in the pumping chamber and a substantially lower pressure in the fluid reservoir which exceeds the threshold value of the pressure difference, so that the check valve opens and allows the pressure chamber to become filled with medically liquid from the exchangeable reservoir.

A valve type that may be designed to operate with such a threshold pressure difference is a ball valve pre-loaded with a spring. The spring pushes the ball into its seat, and only if the pressure acting against the spring force exceeds the latter, the ball valve opens. Other valve types which—depending on their construction—may operate with such a threshold pressure difference are duckbill valves or flap valves.

The advantage of such a valve operating with a threshold pressure difference is that the reservoir can be kept closed until active use is being made of the inhalation device, thus reducing unwanted splashing of medically active liquid stored in the cartridge system during device transport, or evaporation during long-term storage of the device.

In further specific embodiments, the inhalation device of the system according to the invention further may comprise an outlet valve inside the riser pipe, or at an end of the riser pipe, for avoiding a return flow of liquid or air from the riser pipe into the hollow cylinder. In many cases, the use of such outlet valve will prove to be advantageous. Typically, the downstream end of the riser pipe is located close to the nozzle. The nozzle is in fluidic communication with the outside air. After emitting, in aerosolised form, the amount of medically active liquid which is delivered from the pumping unit through the nozzle, driven by the propulsive longitudinal movement of the cylinder, the pumping chamber must be refilled. For this purpose, it slides back on the riser pipe into its previous upstream position (i.e. performs a repulsive longitudinal movement), so that the interior volume of the pumping chamber increases. Along with this, a relative negative pressure (sometimes also referred to as "under-pressure") is generated inside the pumping chamber which causes liquid to be sucked into the pumping chamber from the exchangeable reservoir which is located upstream of the pumping chamber. However, such relative negative pressure may also propagate downstream through the riser pipe up to the outside of the nozzle and could lead to air being sucked into the device through the nozzle, or nozzle openings, respectively. This problem can be avoided by providing an outlet valve, also referred to as outlet check valve, which opens towards the nozzle openings and blocks in the opposite direction.

Optionally, the outlet valve is of a type that blocks below (and opens above) a threshold pressure difference as described in the context of the inlet valve above. If a ball valve with a spring is used, the spring force must be directed against the pumping chamber such that when the difference between the interior pressure of the pumping chamber and the ambient pressure exceeds the threshold pressure difference value, the outlet valve opens. The advantages of such a valve correspond to the respective aforementioned advantages.

As mentioned, the outlet valve may be positioned within the riser pipe as described above. Alternatively, the inhalation device comprises an outlet valve which is not integrated within the riser pipe but positioned at or near one of the ends of the riser pipe, in particular at or near its downstream end, e.g., in a separate connector between the riser pipe and the nozzle. This embodiment may be advantageous in certain cases, e.g., if there is a need for a riser pipe with a particularly small diameter which makes the integration of a valve difficult. By accommodating the outlet valve downstream of the riser pipe, a valve with a relatively large diameter may be used, thus simplifying the requirements for the valve design.

In a further alternative embodiment, the outlet valve is absent. This embodiment may be feasible as the fluid channels of an impingement-type nozzle may have relatively small cross sections, resulting in only minor or very slow back flow of the medically active liquid at the given pressure conditions during the priming of the inhalation device. If the amount of backflow is considered acceptable in view of a particular product application, the inhaler design may be simplified by avoiding the outlet valve.

In any case, whether the inhalation device is designed with or without an outlet valve, all other options and preferences described with respect to other device features are applicable to both of these alternative embodiments.

The exchangeable reservoir for holding the medically active liquid comprised by the inhalation device system of the present invention is provided in form of a cartridge system. The cartridge system of the present invention has an overall volume $V_o$, wherein the term "overall volume" as used herein means the cubage of the entire cartridge system including all components thereof such as the outer walls of the cartridge system. The overall volume $V_o$ of the entire cartridge system, in typical embodiments, may be selected within the range from about 0.1 mL to about 100 mL, or from about 0.1 mL to about 50 mL or from about 0.2 mL to about 30 mL, such as from about 2.5 mL to about 20 mL, or from about 5 mL to about 15 mL.

The exchangeable cartridge system of the present invention has an upstream end and a downstream end and comprises a container portion having an effective volume $V_e$ for holding the medically active liquid and a connection port adapted to releasably and fluidically connect the cartridge system to the pumping unit, specifically via the connection unit of the receiving unit of the inhalation device.

The container portion of the present exchangeable cartridge system, in typical embodiments, has an effective volume $V_e$ selected within the range of from about 0.1 to about 50 mL, or from about 0.1 mL to about 25 mL, or from about 1 mL to about 15 mL, or from about 1 to about 10 mL, specifically from about 3 mL to about 6 mL, or from about 6 mL to about 9 mL, more specifically from about 4.0 mL to about 5.0 mL or from about 7.0 mL to about 8.0 mL.

In specific embodiments, the connection port of the container portion may be in the form of a cap, such as a cap mounted on the downstream end of the container portion. The connection port may have an opening that allows for establishing a fluid connection to the inner lumen of the container portion and to the medically active liquid contained therein. The term "effective volume" means the cubage of the entire container portion including all components thereof such as the outer walls of the container portion or the connection port, such as a cap. The term "lumen" or "inner lumen" as used herein in connection with a hollow body such as the container portion, the extension element, or others means the inner space or cavity inside such hollow body irrespective of whether or not such inner space or cavity is completely or only partially surrounded by the outer walls of said hollow body.

In further specific embodiments, the container portion of the present exchangeable cartridge system may be in the form of a flexible container or in the form of a rigid or, in other words, dimensionally stable container. The terms "rigid" or "dimensionally stable" as used herein means that the container portion does not change its shape or volume when medically active liquid contained therein is discharged from the container during standard operation of the present inhalation device system or, in other words, when the medicinal active liquid is withdrawn from the container portion by the pumping unit during nebulization and administration of the medically active liquid. In specific embodiments of the present inhalation device system, the container portion of the present exchangeable cartridge system is in the form of a dimensionally stable container. In further specific embodiments, the container portion of the present exchangeable cartridge system is in the form of a dimensionally stable container comprising a flexible or collapsible inner container as described in further detail below, wherein the inner container contains the medically active liquid to be administered by the inhalation device system of the present invention.

Generally, the container portion, especially when provided in dimensionally stable form, may have any suitable shape that allows for the introduction of the container portion or the whole exchangeable cartridge system comprising such container portion into the inhalation device of the present inhalation device system. In specific embodiments, suitable shapes comprise but are not limited to bottle-type or tubular or cylindrical shapes, wherein symmetrical as well as non-symmetrical shapes can be implemented. Especially with regard to the axial symmetry of the container device or the entire cartridge system with regard to the main rotational axis of the container device or cartridge system connecting the center of its upstream end with the center of its downstream end, this may allow for advantageous embodiments in which the container device or cartridge system may or may not be inserted into the inhalation device in specific orientations only. In preferred embodiments, however, the inhaler device or entire cartridge system may have a substantially circular cross-sectional shape such that the container device or cartridge system may be introduced into the inhalation device independent of the rotational orientation around the longitudinal main axis.

In further embodiments, the container portion may be in the form of a bottle with a (main) opening, preferably at its downstream end, for charging or discharging the medically active liquid to be stored and administered. It should be noted, however, that the container portion may comprise further (minor) openings, e.g., for ventilation purposes.

In further specific embodiments, the extension element of the present exchangeable cartridge system may be in the form of a rigid or, in other words, dimensionally stable container or hollow body. The terms "rigid" or "dimensionally stable" as used herein in connection with the extension element means that the extension element does not change its shape or volume during standard operation of the present inhalation device system or, in other words, when the medicinal active liquid is withdrawn from the container portion by the pumping unit during nebulization and administration of the medically active liquid. In specific embodiments of the present inhalation device system, the extension element of the present exchangeable cartridge system is in the form of a dimensionally stable hollow body or container.

In further specific embodiments, both, the container portion of the present exchangeable cartridge system as well as the extension element are provided in dimensionally stable form, such as in form of a dimensionally stable container element or hollow body.

Generally, both, the container portion as well as the extension element, especially when provided in dimensionally stable form, may have any suitable shape that allows for the introduction of the container portion or the whole exchangeable cartridge system comprising such container portion into the inhalation device of the present inhalation device system. In specific embodiments, suitable shapes comprise but are not limited to bottle-type or tubular or cylindrical shapes, wherein symmetrical as well as non-symmetrical shapes can be implemented. Especially with regard to the axial symmetry of the container device or the entire cartridge system with regard to the main rotational axis of the container device or cartridge system connecting the center of its upstream end with the center of its downstream end, this may allow for advantageous embodiments in which the container device or cartridge system may or may not be inserted into the inhalation device in specific orientations only. In preferred embodiments, however, the inhaler device or entire cartridge system may have a substantially circular cross-sectional shape such that the container device or cartridge system may be introduced into the inhalation device independent of the rotational orientation around the longitudinal main axis.

In further embodiments, the container portion may be in the form of a bottle with a (main) opening, preferably at its downstream end, for charging or discharging the medically active liquid to be stored and administered. It should be noted, however, that the container portion may comprise further (minor) openings, e.g., for ventilation purposes.

In further specific embodiments, the extension element as well as the container portion, independently of each other, and especially when provided in dimensionally stable form as described above, may be provided in form of a container or hollow body which comprises at least one elastic portion. The term "elastic" as used herein in this context means that at least a portion of the container or hollow body of the extension element and/or container portion may be reversibly deformed by application of an external force especially to the outer walls of such container or hollow body whereby the temporarily deformed container or hollow body relaxes back to its original shape after removal of the external force applied to extension element or container portion. For example, the container portion and/or the extension element may be provided in dimensionally stable form and may comprise a portion or region which may be deformed by a user by squeezing, e.g., by manually squeezing such portion or region of the container portion and/or extension element. This may be useful, for example, for attaching the extension element to the container portion as described in further detail below.

In specific embodiments, the container portion and the extension element are provided in dimensionally stable form and comprise at least one elastic portion. In other embodiments, both, the container portion as well as the extension element are provided in dimensionally stable form and only the container portion or the extension element comprises at least one elastic portion. Preferably, the container portion and the extension element are provided in dimensionally stable form and only the extension element comprises at least one elastic portion. In further embodiments, however, the container portion and the extension element are provided in dimensionally stable form and only the container portion comprises at least one elastic portion.

In specific embodiments, the container portion of the exchangeable reservoir may comprise an inner container, holding the medically active liquid and having a maximum inner volume $V_i$. The term "inner volume" ($V_i$) as used herein in connection with the container portion means the total inner volume of the container portion that can be filled (partially or completely) with a liquid, specifically the medically active liquid to be administered by the inhalation device system according to the present invention. Accordingly, the inner volume $V_i$ of a container portion completely filled with a medically active liquid corresponds to the volume of the medically active liquid contained in such completely filled container portion. In typical embodiments, the maximum inner volume $V_i$ roughly corresponds to the effective volume $V_e$ of the container portion and may be preferably selected within the range of from 0.1 to about 15 mL, or from about 1 to about 10 mL, specifically from about 3 mL to about 6 mL, or from about 6 mL to about 9 mL, more specifically from about 4.0 mL to about 5.0 mL or from about 7.0 mL to about 8.0 mL. In further embodiments, however, the maximum inner volume $V_i$ of an optional inner container may be smaller than the effective volume $V_e$ of the container portion, resulting in situation in which not the entire lumen of the container portion is filled with an optional inner container.

For example, the inner container that may be contained in the container portion of the reservoir may be designed to be collapsible, such as by means of a flexible or elastic wall. The effect of such design is that upon repeated use of the device which involves progressive emptying of the reservoir, the flexible or elastic wall buckles or folds such as to reduce the internal volume of the reservoir, so that the negative pressure which is necessary for extraction of a certain amount of liquid is not required to increase substantially over the period of use. In particular, the optional inner container of the exchangeable reservoir may be designed as a collapsible bag. The advantage of a collapsible bag is that the pressure inside the reservoir is almost independent of the filling level, and the influence of thermal expansion is almost negligible. Also, the construction of such a reservoir type is rather simple and already well established. In further embodiments, however, the inner container may have a non-flexible or rigid form wherein pressure equalization with the surrounding atmosphere during administration of the medically liquid stored therein is achieved by other means, such as inlet valves or a movable piston.

The cartridge system of the inhalation device system of the present invention further comprises an extension element which has an additional volume $V_a$. In preferred embodiments, the sum of the effective volume $V_e$ of the container portion and the additional volume $V_a$ of the extension element equals the overall volume $V_o$ of the cartridge system as described above, specifically in an assembled state as described in further detail below. In specific embodiments, the effective volume $V_e$ corresponds to the entire inner volume of the container portion and the additional volume $V_a$ corresponds to the entire inner volume of the extension element. The additional volume $V_a$ of the extension element, in typical embodiments, may be selected within a range of from about 0.1 mL to about 100 mL, as necessary in view of the specific overall length $L_o$ of the cartridge system and the chosen effective volume $V_e$ of the container portion. In specific embodiments, the additional volume $V_a$ of the extension element may be chosen within the range of from about 0.1 mL to about 25 mL, or from about 0.1 mL to about 10 mL, or from about 0.2 mL to about 5.0 mL, or from about 0.5 mL to about 3.5 mL. The extension element may be attached to the outer surface of the container portion, or more specifically is attached to the outer surface of the container portion as described in further detail below.

In further embodiments, the exchangeable cartridge system has an overall length $L_o$ corresponding to the lengths of the exchangeable cartridge system as measured from the upstream end to the downstream end of the cartridge system in an assembled state or, in other words, in a state in which the container portion is attached to the extension element of the cartridge system. In further embodiments, the container portion has an effective length $L_e$ as measured from the upstream end to the downstream end of the container portion. In yet further embodiments, the extension element has a length $L_a$ (additional length) as measured from the upstream end to the downstream end of the extension element. In typical embodiments, the effective length $L_e$ of the container portion may be selected within a range of from about 0.5 cm to about 20 cm, or from about 1 cm to about 15 cm, or from about 2.5 cm to about 10 cm, or from about 4.0 cm to about 8.0 cm. In further typical embodiments, the additional length $L_a$ of the additional length of the container portion may be selected within a range of from about 0.5 cm to about 19.5 cm, or from about 1.5 cm to about 10 cm, or from about 2.5 cm to about 5.0 cm.

In specific embodiments, in the assembled state, i.e., in a state in which the extension element as attached or affixed to the outer surface of the container element, the overall length $L_o$ of the resulting exchangeable cartridge system equals to the sum of the effective length $L_e$ of the container portion and the additional length $L_a$ of the extension element. Furthermore, it should be pointed out, that the relevant lengths and volumes of the elements of the cartridge system are to be understood as the corresponding values in the assembled state. In the disassembled state, these values can differ due to optional additional components or structures that might be necessary to attach the elements to each other as described in further detail below.

In specific embodiments, the receiving unit of the inhalation device may be adapted to receive or to fully receive and fluidically connect to the exchangeable cartridge system as described above. In these cases, the receiving unit is preferably adapted to receive an exchangeable reservoir having a defined overall length $L_o$ and an overall volume $V_o$ and wherein the exchangeable reservoir is provided in form of a cartridge system having a defined overall length $L_o$ and an overall volume $V_o$ as described above. In these cases, it may be advantageous that the exchangeable reservoir comprises a container portion having an effective length $L_e$ and an extension element having an additional length $L_a$, and wherein the sum of the effective length $L_e$ of the container portion and the additional length $L_a$ of the extension element equals the overall length $L_o$ of the cartridge system (in an assembled state).

This allows for the use of an exchangeable cartridge system in which the length of the container portion $L_e$ and the length of the extension element $L_a$ can be varied according to a specific effective volume needed as long as the overall length $L_o$ of the cartridge system in the assembled state corresponds to overall length of the cartridge system that can be introduced in and received by the receiving unit of the inhalation device. This may be especially advantageous in cases in which an inhalation device may be used with different cartridge systems having the same overall length $L_o$ but with different combinations of a container portion with a specific effective length $L_e$ and an extension element with a specific additional length $L_a$ of the extension element, such as cartridge systems holding different medically active liquids or different amounts of a specific medically active liquid. In these cases, it might be advantageous to provide for a cartridge system that allows for the adaption of the effective volume $V_e$ according to the individual amounts of medically active liquid to be stored therein. Furthermore, it might be advantageous to provide for an inhalation device system and corresponding inhalation device which offers to possibility to receive a cartridge system with an effective volume that may be freely chosen depending on the medically active liquid or amount thereof to be administered.

As described above, the extension element may be attached to the outer surface of the container element. The terms "attached to" or "affixed to" as used in this context herein mean that that the respective parts are attached or affixed to each other in such a way as to substantially prevent their movement relative to each other upon standard operation. In other words, two parts that are affixed or attached to each other may only be movable together, and with respect to each other, they are non-movable or immobile under standard use conditions. In case of the extension element being attached or affixed to the container portion, this means that the resulting cartridge system can be at least introduced into the receiving unit of the inhalation device without disassembly of the cartridge system.

In specific embodiments, the extension element of the cartridge system is permanently attached to the outer surface of the container portion. The terms "permanently attached" or "permanently affixed" as used herein in this context means that the extension element is attached or affixed to the container element in such a way that the two components may not be detached or removed from each other without destruction of a permanent physical connection between the two elements so that the connection may not be restored without further technical means, tools or other aids. For example, a permanent connection may be achieved by gluing, welding or soldering (in case of metallic components).

In alternative specific embodiments, the extension element of the cartridge system is removably attached, or in other words, detachably attached to the outer surface of the container portion. The terms "removably attached" or detachably attached" as used herein in this context means that the physical connection between the container portion and the extension element can be established and released by a user without the use of further technical means, tools or other aids. In specific embodiments, the connection between the container portion and the extension element can be established and reversed only once. In alternative embodiments, the connection between the container portion and the extension element can be established and reversed repeatedly. In further specific embodiments, the extension element can be removed from the container portion without damaging or destructing the extension element or the container portion or both, so that the connection between the extension element and the container portion can be re-established as described in further detail below.

In specific embodiments, the extension element may be affixed or attached to only a part of the outer surface or to a connecting structure (such as a sticky or glued area, a thread or a hook-and-loop fastener element) located at the outer surface of the container portion to form the cartridge system of the present invention. In more specific embodiments, the extension element may be attached or affixed to a part of the outer surface of the container portion located at the upstream end of the container portion especially in cases in which the container portion is provided in the form of a bottle with a (main) opening, preferably at its downstream end, for charging or discharging the medically active liquid to be stored and administered.

In specific embodiments, the extension element is attached to the outer surface of the container portion by a force-fit or form-fit connection, such as by a snap fit-connection. In these cases, both, the container portion and the extension element comprise corresponding structures or elements, such as rings or protrusions or corresponding indentations that allow for the establishment of a form-fit or snap-fit connection. Depending on the physical force necessary to establish or reverse such a force-fit, form-fit or snap-fit connection, such connection may be permanent or reversible or, in other words, removably as described above. In case of a generally reversible, non-permanent connection between extension element and the container portion of the cartridge system it may be advantageous that the force necessary to detach and remove the extension element from the outer surface of the container portion is higher than the force needed to remove the cartridge system from the receiving unit of the inhalation device. This allows for the removal of the cartridge system from the receiving unit of the inhalation device, e.g., by pulling the cartridge system out of the receiving unit of the inhalation device, especially in cases in which the cartridge system may be introduced or inserted from the upstream end of the inhalation device in a downstream direction along a longitudinal main axis of the inhalation device.

In alternative embodiments, however, it may be beneficial that the force needed to remove the extension element from the container portion is lower than the force needed to remove the cartridge system from the receiving unit or the connection unit of the inhalation device, respectively. This allows for the selective removal of the extension element from the receiving unit wherein the container portion stays in the receiving unit of the inhalation device.

In further exemplary embodiments, the connection between the extension element and the container portion may be established by other reversible fastening means or materials such as detachable adhesives, magnetic forces, hook-and-loop fasteners, screw threads, Luer-type locks and others. In these embodiments, however, it might be advantageous that the container portion and/or the extension element is provided in dimensionally stable form, without, however, having a flexible portion.

In specific embodiments, the exchangeable cartridge system of the present inhalation device system (in the assembled state) may have a generally cylindrical shape with a central longitudinal axis connecting the connection port of the container portion located at the downstream end of the cartridge system with the bottom of the cartridge system located at the opposite upstream end of the cartridge system.

In further specific embodiments, the container portion has an upstream end and a downstream end, and the connection port of the container portion may be located at the downstream end of the container portion and the extension element may be attached to the upstream end of the container portion, preferably by a force-fit, form-fit or snap-fit connection.

The container portion of the cartridge system, in specific embodiment may be made or manufactured from a polymeric material, specifically from a thermoplastic polymer, such as polyethylene, polypropylene, polyoxymethylene (POM), polystyrene and others. In alternative embodiments, the container portion may be made of a metal such as stainless steel, aluminum or other suitable metals or mixtures thereof. In preferred embodiments, however, the container portion is made of polyethylene or polypropylene, preferably polypropylene. It should be noted, however, that separate structures of the container portion, such as the connection port, preferably in form of a cap, may be formed from the same or another metallic or non-metallic material as described above.

The extension unit of the cartridge system, in specific embodiments, may have substantially the same cross-sectional diameter as the container portion of the cartridge system, especially with regard to the upstream end of the container portion and the downstream end of the extension element which is beneficial especially in cases in which the two elements are attached or affixed to each other by a form-fit, force-fit or snap-fit connection. However, further embodiments are possible in which in which the container portion has a smaller cross-sectional diameter than the extension element, for example in cases in which the container portion is attached or affixed to the extension element by introduction (e.g., of the upstream end of the container portion) into an opening in (e.g., the downstream end) of the extension element. In further embodiments, the opposite configuration is possible in which the container portion has a larger cross-sectional diameter than the extension element, for example in cases in which the container portion is attached or affixed to the extension element by introduction (e.g., of the downstream end of the extension element) into an opening in (e.g., the upstream end) of the container portion.

In general, the cartridge system may have a symmetrical or non-symmetrical cross-sectional shape. In cases in which it might be important that the cartridge system can only be introduced or received in the receiving unit of the inhalation device in a specific orientation only, a non-symmetrical cross-section may be advantageous. On the other hand, especially to facilitate the insertion of the cartridge system, e.g., for infants or impaired users, it might be beneficial that the cartridge system has a symmetrical cross-section, such as a circular cross-section (perpendicular to the main central axis connecting the downstream end with the upstream end of the exchangeable cartridge system). Accordingly, in specific embodiments, both, the extension element and the container portion of the cartridge system have a circular cross-section. In further embodiments, the container portion and/or the extension element may have constant diameters throughout resulting in a cylindrical cartridge after assembly. In alternative embodiments, however the container unit and/or the extension element may have other cylindrical shapes with varying diameters, especially in case of the extension element that may be broadened in diameter, especially toward the upstream end of the extension element.

In specific embodiments, the extension element of the cartridge system, as well, has an upstream end (i.e., corresponding to the upstream end of the cartridge system) and a downstream end, and may have an opening at the downstream end, the opening having an inner diameter corresponding to the outer diameter of the upstream end of the container portion. As outlined above, especially in cases in which the extension element is to be attached to the container portion by form-fit or snap-fit connection it may be beneficial that additional structures like corresponding protrusions or indentations are provided at the contact surfaces. In further embodiments in which the extension element is to be attached to the container portion by force-fit connection it may be beneficial that no such additional structures are present. For example, in cases in which the upstream end of the container portion is to be introduced into a corresponding opening on the downstream end of the extension element, wherein such opening has an inner diameter matching to the outer diameter of the (upstream end) of the container portion.

The extension element, in specific embodiments may be made of the same material as described above for the container element or from a different material. In both cases, however, the extension element may be made of polymeric material, specifically a thermoplastic polymer such as polyethylene, polypropylene, polyoxymethylene (POM), polystyrene and others. It may be advantageous, in specific embodiments, to use polyethylene or polypropylene, especially polypropylene.

The extension element of the cartridge system, in specific embodiments, may be a hollow body with a hollow space or inner lumen or may be a filled body without an inner space. In preferred embodiments, however, the extension element of the cartridge system may be a hollow body having at least one inner space or cavity contained therein. In these cases, especially when the container portion is provided in the form of a (substantially) closed container and the extension element is provided in the form of a hollow body with a hollow inner space, the resulting cartridge system comprises at least two separate spaces or compartments within the cartridge system that allow for the storage of different components of the present inhalation device system. Furthermore, in further embodiments it is possible that e.g., the extension element comprises two or mor distinct hollow spaces or cavities.

The at least one inner space or cavity, in specific embodiments may contain further elements of functional or nunfunctional nature. The term "functional element" as used herein in this context means an element that is necessary for or allows to generate a functionality of the extension element or cartridge system other than the storage of the medically active liquid to be dispensed by the present inhalation device system.

In specific embodiments, the extension element may be a hollow body without functional elements contained therein. In alternative embodiments, however, the extension element of the cartridge system may comprise a functional element or a plurality of functional elements contained within the inner space of the extension element. In exemplary, non-limiting embodiments, such functional elements may be selected from the group consisting of an indicator device, a blocking mechanism, an electronic interface, such as a Bluetooth interface, an electronic coding system, an electronic data logger, a coding element such as an RFID tag or chip, a pressure reservoir, instruction means, visualization elements, electro-mechanical interfaces, a display and others. Especially in cases in which the inner space or cavity of the extension element contains an indicator device, a blocking element or comparable functionality, said inner space may comprise mechanical elements such as gear units, drive elements such as drive shafts, cogwheels, pushbuttons and the like. This allows for the effective use of the space or volume corresponding to the inner space or lumen of the extension element and allows for the introduction of further functionality into the inhalation device system without, in many cases, the need to enlarge the overall size of the preferably hand-held inhalation device system.

On the other hand, it may be advantageous that the extension element does not comprise any functional elements, especially in cases in which the extension element may be subject to potentially damaging conditions such as exposure to reactive gases or radiation during sterilization. Accordingly, in specific embodiments, the extension element of the cartridge system does not comprise a functional element, especially not an electronic device or interface. In further specific embodiments, the extension element does not comprise or contain an indicator device for counting the number of uses of the inhalation device or exchangeable reservoir.

In preferred embodiments as mentioned above, the extension element is a hollow body with an inner space or lumen that opens to one side, specifically to the downstream end of the extension element and is adapted to be affixed or attached to, either permanently or removably, to the container element holding the medically active liquid to be administered. Accordingly, in specific embodiments, the extension element, more specifically the inner space of the extension element, does not comprise the medically active liquid or another compound to be administered. In further specific embodiments, the extension element of the cartridge system has a ventilation opening to connect the inner space or lumen of the extension element to the surrounding atmosphere when attached to the outer surface of the container portion. Especially in cases, in which the cartridge system is to be sterilized before it is filled with the medically active liquid this may be advantageous, as the cartridges system or, more specifically, the container portion and the extension element may be assembled or attached or affixed to each other prior to the filling of the medically active liquid into the container portion, especially in cases in which the sterilization is performed by exposure to a reactive gas such as ethylene oxide, ozone or other gases suitable for sterilization. Accordingly, in specific embodiments the container portion and the extension element are assembled and sterilized prior to the filling of the cartridge system with the medically active liquid.

As outlined above, the cartridge system has an effective volume $V_e$ of the container portion and the additional volume $V_a$ of the extension element. In exemplary embodiments, the ratio of the effective volume $V_e$ of the container portion to the additional volume $V_a$ of the extension element ranges from about 20:1 to about 1:20, specifically from about 10:1 to about 1:10, or from about 5:1 to about 1:5, or from about 2.5:1 to about 1:2.5, or from about 2:1 to about 1:1. As also outlined above, the cartridge system has an effective length $L_e$ of the container portion and the additional length $L_a$ of the extension element. In exemplary embodiments, the ratio of the effective length $L_e$ of the container portion and the additional length $L_a$ of the extension element ranges about 20:1 to about 1:20, specifically from about 10:1 to about 1:10, or from about 5:1 to about 1:5, or from about 2.5:1 to about 1:2.5, or from about 2:1 to about 1:1.

A further advantage of the present inhalation device system is, that the cartridge system comprising a container portion and an extension element and having an overall length $L_o$ and volume $V_o$ can be replaced by a corresponding (standard) cartridge of the same overall length $L_o$ and volume $V_o$ but without an extension element, i.e., a cartridge which comprises only a container element. This modular design allows for maximum flexibility with regard to the compatibility of the present inhalation device system, or more specifically the inhalation device of the present system which may or may not be used with standard replacement cartridges of a defined length and volume which do not have a removable or non-removable extension element. Accordingly, in specific embodiments of the present inhalation device system the cartridge system can be replaced by a cartridge system without an extension element.

In further embodiments, the exchangeable cartridge system may be also attached to the housing of the inhalation device, or more specifically, to a part of the housing. For example, the cartridge system may be attached or affixed to the removable lower part of the housing. More specifically, the exchangeable cartridge system may be attached to the lower part of the housing via the extension element. This connection may, for example, be established between the outer surface of the extension element and the inner surface of the housing, specifically of the removable lower part of the housing, wherein the term "inner surface" means the surface facing the interior of the housing or inhalation device. The optional connection between the exchangeable cartridge system and the housing, specifically the lower part of the housing wherein the extension element of the cartridge system may be a permanent or a removable connection. Accordingly, in some embodiments, the extension element of the cartridge system may be removably attached to the housing of the inhalation device, such as by a force-fit or form-fit connection as described above. In alternative embodiments, the extension element of the cartridge system may be permanently attached or affixed to the housing, preferably to the removable part of the hosing.

In preferred embodiments, however, the extension element may be removably attached to the housing of the inhalation device. This may be advantageous as it allows for the exchange of a specific extension element, i.e., of an extension element with a specific additional length and volume, by another extension element with a different additional length and volume as may be needed to adapt to a container portion of a given size. In this case also, this allows for a modular design of the present inhalation device system that can be operated with different cartridge systems and container portions adapted to the amount and nature of the medically active liquid to be stored therein.

In further preferred embodiments in which the extension element is removably attached to both, the container unit as well as the housing, specifically the removable lower part of the housing, it may be advantageous that the force needed to remove the extension element from the container portion and the force needed to remove or disconnect the extension element from the housing are higher than the force needed to remove the cartridge system from the receiving of the inhalation device. This allows for the possibility to remove the entire cartridge system from the receiving unit by removing the removable part of the housing from the inhalation device in single operation.

In alternative embodiments, however, it may also be advantageous that the force needed to remove or disconnect the extension element from the housing are lower than the forces needed to remove the extension element from the container portion and the force needed to remove the cartridge system from the receiving unit of the inhalation device. This allows for the possibility to detach the removable part of the housing from the inhalation device without removing the cartridge system from the receiving unit of the inhalation device. In further alternative embodiments, it may be advantageous that the force needed to remove the extension unit from the container portion are lower than the forces needed to detach the container portion from the connection unit of the receiving unit and the force needed to detach or disconnect the extension unit from the removable part of the housing. In these embodiments, it would be possible to remove the removable part of the housing together with the extension unit without, however removing the container portion from the receiving unit if the inhalation device.

In a second aspect, the present invention provides for an exchangeable cartridge system holding a medically active liquid for nebulization and preferably adapted for use in an inhalation device system according to the first aspect of the invention, wherein the cartridge system has an overall volume $V_o$ and comprises a container portion having an effective volume $V_e$ for holding the medically active liquid and a connection unit adapted to releasably and fluidically connect the cartridge system to the pumping unit of an inhalation device, wherein the cartridge system further comprises an extension element having an additional volume $V_a$, the extension unit being attached to the outer surface of the container portion. In preferred embodiments of this second aspect of the invention, the sum of the effective volume $V_e$ of the container portion and the additional volume $V_a$ of the extension element equals the overall volume $V_o$ of the cartridge system (in an assembled state).

In specific embodiments, the exchangeable cartridge system of this second aspect of the invention is especially suitable as an exchangeable reservoir as comprised by the inhalation device system according to the first aspect of the invention.

It should be noted that all embodiments, features and ranges as well as all preferred features, embodiments, ranges as well as combinations thereof as described above in connection with the first aspect of the invention may be applied to or combined with the second aspect of the invention as well as with all further aspects of the invention accordingly.

In a third aspect, the present invention relates to a method for providing an exchangeable reservoir for an inhalation device system of the first aspect of the invention in the form of a cartridge system, specifically in the form of the exchangeable cartridge system of the second aspect of the invention, having an overall volume $V_o$, the method comprising the steps of a) providing a container portion having an effective volume $V_e$ for holding the medically active liquid the container portion comprising a connection port (preferably in form of a cap) adapted to releasably and fluidically connect the cartridge system to the pumping unit of the inhalation device system;

b) providing an extension element having an additional volume $V_a$, preferably wherein the sum of the effective volume $V_e$ of the container portion and the additional volume $V_a$ of the extension element equals the overall volume $V_o$ of the cartridge system (in an assembled state); and c) attaching the extension element to the outer surface of the container portion.

According to step a) of the method of this aspect of the invention, a container portion having an effective volume $V_e$ for holding the medically active liquid the container portion comprising a connection port (preferably in form of a cap) adapted to releasably and fluidically connect the cartridge system to the pumping unit of the inhalation device system is provided.

In preferred embodiments of this third aspect of the invention, the container portion is provided in the form of a dimensionally stable container, more specifically in the form of stable hollow body or container having a connection port (adapted to releasably and fluidically connect the cartridge system to the pumping unit of the inhalation device system) at the downstream end and a surface portion at the opposite upstream end of the container adapted to releasably or permanently, preferably to releasably connect to the extension element.

According to step b) an extension element having an additional volume $V_a$, preferably wherein the sum of the effective volume $V_e$ of the container portion and the additional volume $V_a$ of the extension element equals the overall volume $V_o$ of the cartridge system (in an assembled state) is provided.

In further embodiments of this aspect of the invention, the extension element is provided in form of a dimensionally stable hollow body, preferably with an opening or other connecting means at the downstream end of the extension element. As described in detail above in connection with the inhalation device system of the first aspect of the invention, the extension element may, for example, have an opening or another surface area with fastening means adapted to releasable or permanently, preferably to releasably connect to the container portion. In preferred embodiments, this opening or other fastening means is located at the downstream end of the extension element.

According to step c) of this aspect of the invention the extension element is attached to the outer surface of the container portion. In specific embodiments, the extension element is releasably attached to the outer surface of the container portion, for example by contacting the opening or other connecting means at the surface of the extension element with the corresponding surface portion or connecting means of the container portion. In specific embodiments, the fastening means of the extension element may be manually pressed on the corresponding fastening means or outer surface of the container portion. In alternative embodiments, however, the extension element may be screwed into a corresponding thread on the outer surface of the container portion.

In further specific embodiments, the method of this aspect of the invention further comprises additional step a1) following step a) and followed by step b):

a1) introducing the container portion into the receiving unit of the inhalation device system of the first aspect of the invention and optionally connecting the connection port of the container portion to the pumping unit of the inhalation device system.

In this embodiment, the method further comprises additional step b1) following step b) and followed by step c):

b1) introducing the extension element into the receiving unit of the inhalation device.

DETAILED DESCRIPTION OF THE DRAWINGS

FIG. 1 shows an inhalation device system (10) comprising an inhalation device (20) and an exchangeable reservoir in the form of a cartridge system (30) (wherein the different elements of the cartridge system are not depicted) inserted into the inhalation device. The inhalation device (20) has a housing (21) with a lower part (22) that can be detached from the inhalation device (20) and removed to open the housing (21) and allow access to the receiving unit (23) in which the exchangeable cartridge system (30) can be inserted. The receiving unit (23) further has a connection unit (24) adapted to releasably and fluidically connect to a connection port (32) of the exchangeable reservoir.

The inhalation device (20) further has a nozzle (25) located at the downstream end of the inhalation device for nebulization of the medically active liquid. The inhalation device further has a pumping unit (40) which is arranged within the housing (21). As described in detail above, the pumping unit is fluidically connected to the reservoir (via the connection unit (24) of the receiving unit (23)) and to the nozzle (25) and is adapted to pump the medically active liquid in a downstream direction from the reservoir (30) to the nozzle (25).

The pumping unit (40) has an upstream end (41) that is fluidically connected to the exchangeable reservoir (30); a downstream end (42) that is fluidically connected to the nozzle (25); wherein the pumping unit (40) further comprises (i) a riser pipe (43) having an upstream end (44), wherein the riser pipe (43) is adapted to function as a piston in the pumping unit (40), and wherein the riser pipe (43) is firmly affixed to the user-facing (downstream) side of the housing (21) such as to be immobile relative to the housing (21); and (ii) a hollow cylinder (45) located upstream of the riser pipe (43), wherein the upstream end of the riser pipe (44) is inserted in the cylinder (45) such that the cylinder (45) is longitudinally movable on the riser pipe (43).

As also shown in FIG. 1, the pumping unit (40) comprises (iii) a lockable means for storing potential energy (46) when locked and for releasing the stored energy when unlocked, the means (46) being arranged outside of, and mechanically coupled to, the cylinder (45) such that unlocking the means (46) results in a propulsive longitudinal movement of the cylinder (45) towards the downstream end of the pumping unit (42).

Figure 2:
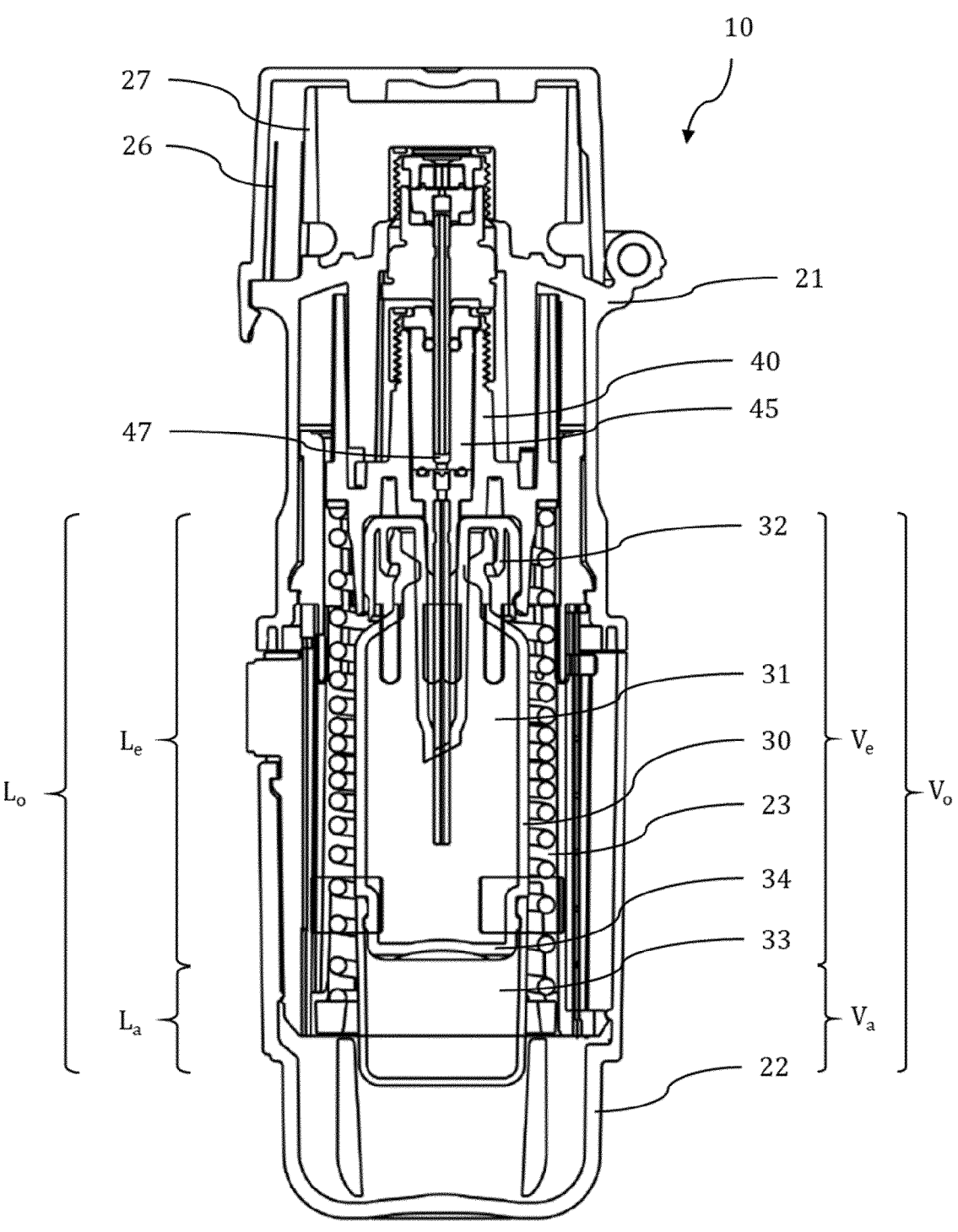
FIG. 2 depicts a cross-sectional view of an inhalation device system with a cartridge inserted into an inhalation device, wherein the cartridge comprises an extension element.

In FIG. 2 the inhalation device system (10) is shown with the same inhalation device (20), however, viewed from a different angle and with reference numbers of elements described for FIG. 1 partly omitted. As can be seen herein, the housing (21) of the inhalation device comprises a cap (26) located on and covering the downstream end (27) or, in other words, the user-facing side of the housing when in a closed state. The housing (21) further has a removable lower part (22) located at the opposite, upstream end of the inhalation device. The removable lower part (22) of the housing, once removed from the inhalation device allows for the access to the receiving unit (23) into which the cartridge system (30) can be inserted or removed by a movement along the longitudinal main axis (A), see FIG. 4.

As also shown in FIG. 2, the exchangeable reservoir (30) in form a cartridge system has a container portion (31) with a connection port (32) in the form of a cap. The container portion (31) may also have an inner container (not shown) such as a flexible bag which may hold the medically active liquid. The connection port (32) is adapted to releasably and fluidically connect the cartridge system (30) to the pumping unit (40). The cartridge system (30) of the inhalation device system (10) further comprises an extension element (33) which is attached to the outer surface of the container portion (31), more specifically to the upstream end (34) of the container portion. As can be seen in FIG. 2, the sum of the effective length $L_e$ of the container portion (31) and the additional length $L_a$ of the extension element (33) equals the overall length $L_o$ of the cartridge system (30) in an assembled state as shown, in this case corresponding to the overall length of the cartridge shown in FIG. 1. As also indicated in FIG. 2, the container portion (31) has an effective volume $V_e$ and the extension element (33) has an additional volume $V_a$ wherein the sum of the effective volume $V_e$ of the container portion (31) and the additional volume $V_a$ of the extension element (33) equals the overall volume $V_o$ of the cartridge system (30) in an assembled state. Furthermore, FIG. 2 (as FIG. 1) shows an inlet check-valve (47) located at the upstream end of hollow cylinder.

FIG. 3 shows a side view of the exchangeable cartridge system (30) in a disassembled state or prior to assembly, respectively. The cartridge system (30) has a container portion (31) with a connection port or unit (32) in the form of a cap located and attached to the downstream end (35) of the container portion (31). The container portion has a generally cylindrical shape. In the shown example, it narrows in diameter at the upstream end (34) of the container portion and has protrusions (36) for establishing a connection to the extension element (33) by form-fit or snap-fit.

FIG. 4 shows a perspective view of the cartridge system (30) of FIG. 3 with a connection port or unit (32) in the form of a cap located and attached to the downstream end (35) of the container portion (31) prior to assembly or after disassembly. As can be seen, extension element (33) is in the form of a hollow body having an opening (37) at the downstream end of the extension element (33) and an inner lumen, space or cavity (39b). On the inner surface of the extension element (33), in the shown example, the opening (37) of the extension element is surrounded by indentations (38) to establish the form- or snap-fit connection to the corresponding protrusions (36) of the container portion (31). It should be noted, however, that in an inverse configuration, indentations can be provided with the container portion while the corresponding protrusions can be provided with the extension element. In any case, the connection may be established, for example, by manually pressing the opening (37) or, in other words, downstream end of the extension element (33) on the upstream end (34) of the container portion (31). It should be noted that, depending on the specific shape and structure of the protrusions (36) and indentations (38) a form- or snap-fit connection may be established which is either permanent or which can be reversed, e.g., by manually removing or pulling apart the extension element (33) from the container portion (31). As can also be seen in FIG. 4, the extension element has a small ventilation opening (39) which establishes a fluidic connection between the inner lumen (39b) of the extension element (33) and the surrounding atmosphere after assembly of the cartridge system (30).

Furthermore, FIG. 4 shows the longitudinal main axis (A) connecting the center of the downstream end of cartridge system in the form of cap (32) with the center of the upstream end of the cartridge system, more specifically, with the center of the upstream end of the extension element (33).

FIG. 5 shows the cartridge system (30) in an assembled state in which the container portion (31) with a connection port or unit (32) in the form of a cap (32) having an effective length $L_e$ is attached or affixed to the extension element (33) having an additional length $L_a$. As can be seen, in this example the resulting cartridge system (30) has a generally cylindrical shape with the container portion (31) and the extension element (33) having the same diameter. Due to the ventilation opening (39) the assembled cartridge system (30) can be sterilized by gas-sterilization prior to filling the medically active liquid into the container portion (31) or the inner container, if present, respectively.

Figure 6:
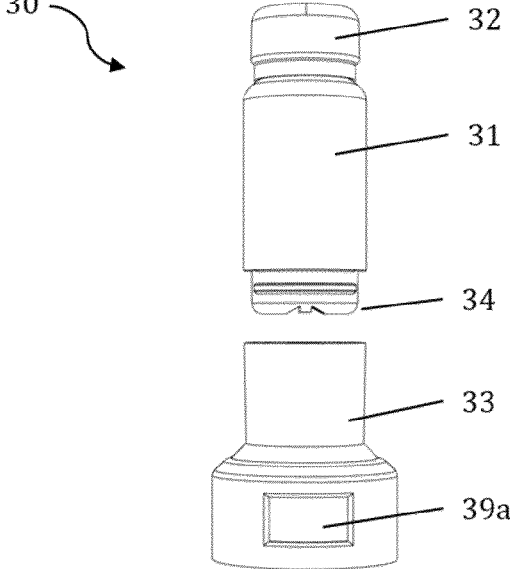
FIG. 6 depicts a different cartridge system with an extension element having an enlarged diameter in the disassembled state.

FIG. 6 depicts another example of a cartridge system (30) with an extension element (33) having an enlarged diameter in the disassembled state. In this example, the extension element (33) has at its downstream end a diameter that corresponds to the diameter of the upstream end (34) of the container portion (31) for establishing the form-fit or snap-fit connection. In this example, the extension element (33) has—due to the partly enlarged diameter—a higher additional volume $V_a$ (as compared to an extension element (33) having the same diameter as the container portion (31) which may be advantageous, especially in cases in which one or more functional elements such as an indicator device, a blocking mechanism, an electronic interface, an electronic coding system, an electronic data logger, a coding element, a pressure reservoir, instruction means, and others are to be located in the extension element (33). The shown extension element (33) further has a further opening in form of a window (39a) to allow physical or visual access to the functional elements optionally located in the extension element (33).

Figure 7:
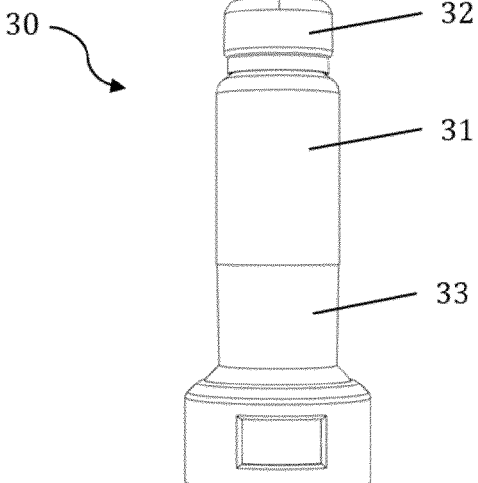
FIG. 7 depicts a different cartridge system with an extension element having an enlarged diameter in the assembled state.

FIG. 7 depicts the cartridge system (30) of FIG. 6 in the assembled state.

LIST OF REFERENCE NUMERALS

10 Inhalation device system
20 Inhalation device
21 housing
22 lower part of housing
23 receiving unit
24 connection unit
25 nozzle
26 cap
30 exchangeable cartridge system
31 container portion
32 connection port
33 extension element
34 upstream end of the container portion
35 downstream end of the container portion
36 protrusion
37 opening of the extension element
38 indentations
39 ventilation opening
39a window
39b inner space, lumen of the extension element
40 pumping unit
41 upstream end of the pumping unit
42 downstream end of the pumping unit
43 riser pipe
44 upstream end of the riser pipe

45 hollow cylinder of pumping unit
46 lockable means for storing potential energy
47 inlet check-valve
A central axis of the cartridge system
$L_e$ effective length of the container portion
$L_a$ additional length of the extension element
$L_o$ overall length of the cartridge system
$V_e$ effective volume of the container portion
$V_a$ additional volume of the extension element
$V_o$ overall volume of the cartridge system The following is a list of numbered embodiments E1 to E30 comprised by the present invention:

E1. Inhalation device system (10) for the inhalative administration of a medically active liquid in nebulized form, the system comprising an inhalation device (20) and an exchangeable reservoir (30) for holding the medically active liquid, wherein the inhalation device (20) comprises a housing (21) having a receiving unit (23), the receiving unit having a connection unit (24) adapted to releasably and fluidically connect to a connection port (31) of the exchangeable reservoir (30), the receiving unit (24) being adapted to receive and fluidically connect to the exchangeable reservoir (30);

a nozzle (25) for nebulization of the medically active liquid; and a pumping unit (40) arranged within the housing (21) and adapted to be fluidically connected to the reservoir (30) and to the nozzle (25) and being adapted to convey the medically active liquid in a downstream direction from the reservoir (30) to the nozzle (25);

wherein the exchangeable reservoir (30) is provided in form of a cartridge system having an overall volume $V_o$ and comprising a container portion (31) having an effective volume $V_e$ for holding the medically active liquid and a connection port (32) adapted to releasably and fluidically connect the cartridge system (30) to the pumping unit (40), wherein the cartridge system (30) further comprises an extension element (33) having an additional volume $V_a$, the extension element (33) being attached to the outer surface of the container portion (31).

E2. The inhalation device system (10) according to embodiment E1, wherein the sum of the effective volume $V_e$ of the container portion (31) and the additional volume $V_a$ of the extension element (33) equals the overall volume $V_o$ of the cartridge system (30).

E3. The inhalation device system (10) according to embodiment E1 or E2, wherein the container portion (31) of the exchangeable reservoir (30) comprises an inner container, holding the medically active liquid and having a maximum volume $V_i$.

E4. The inhalation device system (10) according to any one of the preceding embodiments, wherein the inner container of the container portion (31) is provided in form of a bag, specifically in form of a collapsible bag.

E5. The inhalation device system (10) according to any one of the preceding embodiments, wherein the container portion (31) is provided in dimensionally stable form.

E6. The inhalation device system (10) according to any one of the preceding embodiments, wherein the extension element (33) is provided in dimensionally stable form.

E7. The inhalation device system (10) according to any one of the preceding embodiments, wherein the container portion (31) and the extension element (33) are provided in dimensionally stable form.

E8. The inhalation device system (10) according to any one of the preceding embodiments, wherein the container portion (31) comprises at least one elastic portion.

E9. The inhalation device system (10) according to any one of the preceding embodiments, wherein the extension element (33) comprises at least one elastic portion.

E9. The inhalation device system (10) according to any one of the preceding embodiments, wherein the extension element (33) and the container portion (31) comprise at least one elastic portion.

E10. The inhalation device system (10) according to any one of the preceding embodiments, wherein the extension element and the container portion are provided in dimensionally stable form and wherein the extension element and the container portion comprises at least one elastic portion.

E11. The inhalation device system (10) according to any one of the preceding embodiments, wherein the receiving unit (23) is adapted to receive and fluidically connect to an exchangeable reservoir (30) having a defined overall length $L_o$ and an overall volume $V_o$ and wherein the exchangeable reservoir (30) is provided in form of a cartridge system having a defined overall length $L_o$ and an overall volume $V_o$.

E12. The inhalation device system according to any one of the preceding embodiments, wherein the exchangeable reservoir (30) comprises a container portion (31) having an effective length $L_e$ and an extension element (33) having an additional length $L_a$, and wherein the sum of the effective length $L_e$ of the container portion (31) and the additional length $L_a$ of the extension element (33) equals the overall length $L_o$ of the cartridge system (30) (in an assembled state).

E13. The inhalation device system (10) according to any one of the preceding embodiments, wherein the extension element (33) of the cartridge system (30) is removably attached to the outer surface of the container portion (31).

E14. The inhalation device system (10) according to any one of the preceding embodiments, wherein the extension element (33) is attached to only a part of the outer surface of the container portion.

E15. The inhalation device system (10) according to any one of the preceding embodiments, wherein the extension element (33) is attached to a part of the outer surface of the container portion (31) located at the upstream end of the container portion.

E16. The inhalation device system (10) according to any one of embodiments E13 to E15, wherein the force necessary to remove the extension element (33) from the outer surface of the container portion (31) is higher than the force needed to remove the cartridge system (30) from the receiving unit (23) of the inhalation device (20).

E17. The inhalation device system (10) according to any one of embodiments E1 to E12, wherein the extension element (33) of the cartridge system (30) is permanently attached to the outer surface of the container portion (31).

E18. The inhalation device system (10) according to any one of the preceding embodiments, wherein the exchangeable cartridge system (30) (in the assembled state) has a cylindrical shape with a central longitudinal axis (A) connecting the connection port (32) of the container portion (31) located at the downstream end of the cartridge system (30) with the bottom of the cartridge system (30) located at the opposite upstream end of the cartridge system (30).

E19. The inhalation device system (10) according to any one of the preceding embodiments, wherein the container portion (31) has an upstream end (34) and a downstream end (35) and wherein the connection port (32) is located at the downstream end (34) of the container portion (31) and wherein the extension element (33) is attached to the upstream end (35) of the container portion.

E20. The inhalation device system (10) according to any one of the preceding embodiments, wherein the extension element (33) is attached to the outer surface of the container portion (31) by a force- or form-fit connection.

E21. The inhalation device system (10) according to any one of the preceding embodiments, wherein the extension element (33) has substantially the same cross-sectional diameter as the container portion (31) of the cartridge system (30).

E22. The inhalation device system (10) according to any one of the preceding embodiments, wherein the extension element (33) and the container portion (31) of the cartridge system (30) have a circular cross-section.

E23. The inhalation device system (10) according to any one of the preceding embodiments, wherein the extension element (33) has an opening (37) at the downstream end, the opening having a diameter corresponding to the (outer) diameter of the upstream end (34) of the container portion.

E24. The inhalation device system (10) according to any one of the preceding embodiments, wherein the extension element (33) of the cartridge system (30) is a hollow body without functional elements contained therein.

E25. The inhalation device system (10) according to any one of the preceding embodiments, wherein the extension element (33) does not comprise the medically active liquid or other compound to be administered.

E26. The inhalation device system (10) according to any one of the preceding embodiments, wherein the extension element (33) of the cartridge system (30) has a ventilation opening (39) (to the inner lumen of the extension element (33)) to the surrounding atmosphere when attached to the outer surface of the container portion (31).

E27. The inhalation device system (10) according to any one of the preceding embodiments, wherein the container portion (31) and the extension element (33) are assembled and sterilized prior to the filling of the cartridge system (30) with the medically active liquid.

E28. The inhalation device system according to any one of the preceding embodiments, wherein the extension element (33) comprises a functional element contained within the inner lumen of the extension element (33).

E29. The inhalation device system (10) according to embodiment E28, wherein the functional element is selected from an indicator device, a blocking mechanism, an electronic interface, an electronic coding system, an electronic data logger, a coding element, a pressure reservoir, and instruction means.

E30. The inhalation device system (10) according to any one of the preceding embodiments, wherein the extension element (33) of the cartridge system (30) does not comprise an indicator device for counting the number of uses of the inhalation device or exchangeable reservoir.

E31. The inhalation device system (10) according to any one of the preceding embodiments, wherein the exchangeable cartridge (30) has an overall volume $V_o$ selected within the range of from about 0.2 mL to about 30 mL.

E32. The inhalation device system (10) according to any one of the preceding embodiments, wherein the container portion (31) of the exchangeable cartridge system (30) has an effective volume $V_e$ selected within the range of from about 0.1 to about 15 mL, or from about 1 to about 10 mL, specifically from about 3 to about 6 mL, or from about 6 to about 9 mL, more specifically from about 4.0 to about 5.0 mL or from about 7.0 to about 8.0 mL.

E33. The inhalation device system (10) according to any one of the preceding embodiments, wherein the additional volume $V_a$ of the extension element (33) may be chosen within the range of from about 0.1 ml to about 25 mL or from about 0.2 mL to about 5.0 mL or from about 0.5 mL to about 3.5 mL.

E34. The inhalation device system (10) according to any one of the preceding embodiments, wherein the cartridge system (30) can be replaced by a cartridge system without an extension element.

E35. The inhalation device system (10) according to any one of the preceding embodiments, wherein the pumping unit (40) of the inhalation device (20) comprises
an upstream end that is fluidically connected to the exchangeable reservoir (30);
a downstream end that is fluidically connected to the nozzle (25);
wherein the pumping unit further comprises
(i) a riser pipe (43) having an upstream end, wherein the riser pipe (43) is
adapted to function as a piston in the pumping unit, and
firmly affixed to the user-facing side of the housing (21) such as to be immobile relative to the housing (21); and
(ii) a hollow cylinder (41) located upstream of the riser pipe (44), wherein the upstream end of the riser pipe (43) is inserted in the cylinder (41) such that the cylinder (41) is longitudinally movable on the riser pipe (43).

E36. The inhalation device system (10) according to embodiment 35, wherein the pumping unit (40) comprises
(iii) a lockable means for storing potential energy (46) when locked and for releasing the stored energy when unlocked, the means (46) being arranged outside of, and mechanically coupled to, the cylinder (41) such that unlocking the means (46) results in a propulsive longitudinal movement of the cylinder (41) towards the downstream end of the pumping unit.

E37. An exchangeable cartridge system (30) for holding a medically active liquid for nebulization and adapted for us in an inhalation device system (10) according to any one of the preceding embodiments, wherein the cartridge system (30) has an overall volume $V_o$ and comprises a container portion (31) having an effective volume $V_e$ for holding the medically active liquid and a connection unit (24) adapted to releasably and fluidically connect the cartridge system (30) to the pumping unit (40) of an inhalation device (20), wherein the cartridge system (30) further comprises an extension element (33) having an additional volume $V_a$, the extension element (33) being attached to the outer surface of the container portion (31).

E38. The exchangeable cartridge system according to embodiment E37, wherein the sum of the effective volume $V_e$ of the container portion (31) and the additional volume $V_a$ of the extension element (33) equals the overall volume $V_o$ of the cartridge system (30) (in an assembled state).

E39. A method for providing an exchangeable reservoir for an inhalation device system according to any one of embodiments E1 to E36 in the form of a cartridge system, specifically in the form of the exchangeable cartridge system according to embodiment 37 or 38 having an overall volume $V_o$, the method comprising the steps of a) providing a container portion having an effective volume $V_e$ for holding the medically active liquid the container portion comprising a connection port (preferably in form of a cap) adapted to releasably and fluidically connect the cartridge system to the pumping unit of the inhalation device system;

b) providing an extension element having an additional volume $V_a$, preferably wherein the sum of the effective volume $V_e$ of the container portion and the additional volume $V_a$ of the extension element equals the overall volume $V_o$ of the cartridge system (in an assembled state); and c) attaching the extension element to the outer surface of the container portion.

E40. The method according to embodiment 39, further comprising step a1) introducing the container portion into the receiving unit of the inhalation device system of the first aspect of the invention and optionally connecting the connection port of the container portion to the pumping unit of the inhalation device system.

E41. The method according to embodiment 40, further comprising step b1) introducing the extension element into the receiving unit of the inhalation device.

What is claimed is:

1. An inhalation device system for the inhalative administration of a medically active liquid in nebulized form, the system comprising an inhalation device and an exchangeable reservoir for holding the medically active liquid, wherein the inhalation device comprises a housing having a receiving unit, the receiving unit having a connection unit adapted to releasably and fluidically connect to a connection port of the exchangeable reservoir, the receiving unit being adapted to receive and fluidically connect to the exchangeable reservoir;

a nozzle for nebulization of the medically active liquid; and a pumping unit arranged within the housing and adapted to be fluidically connected to the reservoir and to the nozzle and being adapted to convey the medically active liquid in a downstream direction from the reservoir to the nozzle;

wherein the exchangeable reservoir is provided in form of a cartridge system having an overall volume $V_o$ and comprising a container portion having an effective volume $V_e$ for holding the medically active liquid and the connection port adapted to releasably and fluidically connect the cartridge system to the pumping unit, wherein the cartridge system further comprises an extension element having an additional volume Va, the extension element being attached to an outer surface of the container portion, and an inner container located within and extending through the container portion and into the extension element, the inner container comprising a collapsible bag configured to hold the medically active liquid.

2. The inhalation device system according to claim 1, wherein the sum of the effective volume $V_e$ of the container portion and the additional volume $V_a$ of the extension element equals the overall volume $V_o$ of the cartridge system.

3. The inhalation device system according to claim 2, wherein the exchangeable reservoir comprises the container portion having an effective length $L_e$ and the extension element having an additional length $L_a$, and wherein the sum of the effective length $L_e$ of the container portion and the additional length $L_a$ of the extension element equals the overall length $L_o$ of the cartridge system in an assembled state.

4. The inhalation device system according to claim 1, wherein the extension element of the cartridge system is removably attached to the outer surface of the container portion.

5. The inhalation device system according to claim 1, wherein the extension element is attached to the outer surface of the container portion by a force- or form-fit connection.

6. The inhalation device system according to claim 1, wherein the extension element has substantially the same cross-sectional diameter as the container portion of the cartridge system.

7. The inhalation device system according to claim 1, wherein the extension element of the cartridge system is a hollow body without functional elements contained therein.

8. The inhalation device system according to claim 1, wherein the extension element comprises a functional element contained within an inner lumen of the extension element.

9. The inhalation device system according to claim 1, wherein the extension element of the cartridge system does not comprise an indicator device for counting the number of uses of the inhalation device or exchangeable reservoir.

10. The inhalation device system according to claim 1, wherein the pumping unit of the inhalation device comprises an upstream end that is fluidically connected to the exchangeable reservoir;

a downstream end that is fluidically connected to the nozzle;

wherein the pumping unit further comprises (i) a riser pipe having an upstream end, wherein the riser pipe is adapted to function as a piston in the pumping unit, and firmly affixed to a user-facing side of the housing such as to be immobile relative to the housing; and (ii) a hollow cylinder located upstream of the riser pipe, wherein the upstream end of the riser pipe is inserted in the cylinder such that the cylinder is longitudinally movable on the riser pipe.

11. An inhalation device system for the inhalative administration of a medically active liquid in nebulized form, the system comprising an inhalation device and an exchangeable reservoir for holding the medically active liquid, wherein the inhalation device comprises:

a housing having a receiving unit, the receiving unit having a connection unit configured to releasably and fluidically connect to a connection port of the exchangeable reservoir;

a nozzle for nebulization of the medically active liquid; and a pumping unit arranged within the housing and configured to be fluidically connected to the exchangeable reservoir and to the nozzle and being configured to convey the medically active liquid in a downstream direction from the exchangeable reservoir to the nozzle;

wherein the exchangeable reservoir is provided as a cartridge system, the cartridge system comprising:

a container portion having an effective volume $V_e$ for holding the medically active liquid, an extension element having an additional volume $V_a$, the extension element being attached to the outer surface of the container portion, and an inner container located within and extending through the container portion and into the extension element, the inner container comprising a collapsible bag configured to hold the medically active liquid and having a maximum volume $V_i$ in a range from about 7.0 mL to 8.0 mL;

the container portion comprising the connection port configured to releasably and fluidically connect the exchangeable reservoir to the pumping unit; and the sum of the effective volume $V_e$ of the container portion and the additional volume $V_a$ of the extension element equals an overall volume $V_o$ of the cartridge system.

12. The inhalation device system according to claim 11, wherein the extension element of the cartridge system is permanently attached to the outer surface of the container portion.

13. The inhalation device system according to claim 11, wherein the container portion and the extension element are made of the same material.

14. The inhalation device system according to claim 11, wherein the extension element has substantially a same cross-sectional diameter as the container portion of the cartridge system.

15. The inhalation device system according to claim 11, wherein the extension element has a differing cross-sectional diameter to the container portion of the cartridge system.

16. The inhalation device system according to claim 11, wherein the inhalation device further comprises an outlet valve.

17. The inhalation device system according to claim 11, wherein the inhalation device further comprises an inlet valve.

18. The inhalation device system according to claim 11, wherein the pumping unit of the inhalation device comprises:

an upstream end that is fluidically connected to the exchangeable reservoir;

a downstream end that is fluidically connected to the nozzle; wherein the pumping unit further comprises:

(i) a riser pipe having an upstream end, wherein the riser pipe is configured as a piston in the pumping unit, and firmly affixed to a user-facing side of the housing and is immobile relative to the housing; and (ii) a hollow cylinder located upstream of the riser pipe, wherein the upstream end of the riser pipe is inserted in the cylinder with the cylinder longitudinally movable on the riser pipe.

* * * * *